US011529108B2

(12) United States Patent
Tai et al.

(10) Patent No.: US 11,529,108 B2
(45) Date of Patent: Dec. 20, 2022

(54) METHODS AND APPARATUS FOR IMPROVING THE IMAGE RESOLUTION AND SENSITIVITY OF WHOLE-BODY POSITRON EMISSION TOMOGRAPHY (PET) IMAGING

(71) Applicants: Yuan-Chuan Tai, St. Louis, MO (US); Joseph O'Sullivan, St. Louis, MO (US); Ke Li, St. Louis, MO (US); Qiang Wang, St. Louis, MO (US)

(72) Inventors: Yuan-Chuan Tai, St. Louis, MO (US); Joseph O'Sullivan, St. Louis, MO (US); Ke Li, St. Louis, MO (US); Qiang Wang, St. Louis, MO (US)

(73) Assignee: Washington University, St. Louis, MO (US)

( * ) Notice: Subject to any disclaimer, the term of this patent is extended or adjusted under 35 U.S.C. 154(b) by 10 days.

(21) Appl. No.: 16/697,722

(22) Filed: Nov. 27, 2019

(65) Prior Publication Data

US 2020/0170588 A1 Jun. 4, 2020
US 2021/0196211 A9 Jul. 1, 2021

Related U.S. Application Data

(60) Provisional application No. 62/773,595, filed on Nov. 30, 2018.

(51) Int. Cl.
*G01T 1/29* (2006.01)
*A61B 6/03* (2006.01)
*A61B 6/00* (2006.01)

(52) U.S. Cl.
CPC ............ *A61B 6/037* (2013.01); *A61B 6/4233* (2013.01); *G01T 1/2985* (2013.01)

(58) Field of Classification Search
CPC ....... A61B 6/037; A61B 6/4233; A61B 6/032; A61B 6/4417; A61B 6/5235; A61B 6/582; G01T 1/2985
See application file for complete search history.

(56) References Cited

U.S. PATENT DOCUMENTS 6,490,476 B1 * 12/2002 Townsend .............. A61B 6/032
250/363.03
6,700,949 B2 * 3/2004 Susami ................ A61B 6/4417
250/363.03

(Continued)

OTHER PUBLICATIONS

JP 5-150046 Translation.*

(Continued)

*Primary Examiner* — David P Porta
*Assistant Examiner* — Djura Malevic
(74) *Attorney, Agent, or Firm* — Armstrong Teadale LLP

(57) ABSTRACT

A positron emission tomography (PET) technique that can enhance the image resolution and system sensitivity of a clinical PET/CT scanner for imaging a whole body or a target region of a subject is provided. The system includes a detector array and a detector panel. The detector array includes an array of gamma ray detectors defining a field of view of a scanner and configured to detect at least one coincidence event. The detector panel includes an array of gamma ray detectors having a higher intrinsic spatial resolution than the detector array and positioned in closer proximity to a patient table than the detector array. The detector panel is positioned outside the field of view defined by the detector array during at least a portion of scanning by the PET system. The detector panel is configured to detect at least one coincidence event in cooperation with the detector array. The control unit is configured to control the detector array, the detector panel, and the patient bed to operate in cooperation with each other.

20 Claims, 22 Drawing Sheets

(56) References Cited

U.S. PATENT DOCUMENTS

| | | | | |
|---|---|---|---|---|
| 6,878,941 | B2* | 4/2005 | Balan | A61B 6/4429 250/363.02 |
| 7,154,096 | B2* | 12/2006 | Amano | A61B 6/032 250/363.03 |
| 7,447,345 | B2* | 11/2008 | Shanmugam | A61B 6/032 250/363.03 |
| 8,260,013 | B2* | 9/2012 | Pekar | G06T 7/33 382/128 |
| 8,581,196 | B2* | 11/2013 | Yamaya | A61N 5/1048 250/363.03 |
| 8,594,404 | B2* | 11/2013 | Yamaya | G01T 1/2985 382/131 |
| 8,630,696 | B2* | 1/2014 | Kim | A61B 6/5235 600/427 |
| 9,029,787 | B2* | 5/2015 | Yamaya | G01T 1/1603 250/363.03 |
| 9,817,131 | B2* | 11/2017 | Nathan | A61B 6/4417 |
| 10,413,267 | B2* | 9/2019 | Gagnon | G01N 23/046 |
| 10,478,137 | B2* | 11/2019 | Liu | A61B 5/0035 |
| 10,782,423 | B2* | 9/2020 | Fu | A61B 5/0035 |
| 10,912,528 | B2* | 2/2021 | Corbeil | A61B 6/4417 |
| 2003/0058984 | A1* | 3/2003 | Susami | A61B 6/037 378/19 |
| 2003/0212320 | A1* | 11/2003 | Wilk | A61B 6/5235 600/407 |
| 2006/0124855 | A1* | 6/2006 | Gagnon | G01T 1/2985 250/370.09 |
| 2007/0238950 | A1* | 10/2007 | Vija | A61B 6/037 600/407 |
| 2008/0001089 | A1* | 1/2008 | Lusser | G01T 1/249 250/363.02 |
| 2009/0213983 | A1* | 8/2009 | Vaquero Lopez | G01T 1/1603 378/4 |
| 2009/0226066 | A1* | 9/2009 | Williams | A61B 6/037 382/131 |
| 2010/0046821 | A1* | 2/2010 | Manjeshwar | G06T 11/008 382/131 |
| 2010/0128956 | A1* | 5/2010 | Yamaya | G01T 1/2985 382/132 |
| 2010/0166137 | A1* | 7/2010 | Sawanaga | A61B 6/032 378/4 |
| 2011/0288397 | A1* | 11/2011 | Inoue | A61B 6/0487 600/407 |
| 2012/0046544 | A1* | 2/2012 | Inoue | A61B 6/5235 600/425 |
| 2012/0161014 | A1* | 6/2012 | Yamaya | A61B 6/037 250/363.03 |
| 2013/0003918 | A1* | 1/2013 | Takayama | A61B 6/4417 378/19 |
| 2013/0030287 | A1* | 1/2013 | Yamaya | G01T 1/2985 600/425 |
| 2014/0334702 | A1* | 11/2014 | El Fakhri | G06T 11/005 382/131 |
| 2015/0073272 | A1* | 3/2015 | Corbeil | A61B 6/4417 600/427 |
| 2016/0183890 | A1* | 6/2016 | Nathan | A61B 6/4417 378/9 |

OTHER PUBLICATIONS

Cherry, Simon R., et al., Total-Body PET: Maximizing Sensitivity to Create New Opportunities for Clinical Research and Patient Care. J Nucl Med, Jan. 2018. 59(1): p. 3-12.

Surti, S., et al., Design Study of a Whole-Body PET Scanner With Improved Spatial and Timing Resolution. IEEE Transactions on Nuclear Science, 2013. 60(5): p. 3220-3226.

Wu, H., et al., A Feasibility Study of a Prototype PET Insert Device to Convert a General-Purpose Animal PET Scanner to Higher Resolution. Journal of Nuclear Medicine, Jan. 2008. 49(1): p. 79-87.

Pinker, K., et al., Molecular breast imaging. An update, Radiologe, 2014. 54(3): p. 241-253.

Surti, S., Radionuclide Methods and Instrumentation for Breast Cancer Detection and Diagnosis. Seminars in Nuclear Medicine, 2013. 43(4): p. 271-280.

Janecek, Martin et al., A Simulation Study for the Design of a Prototype Insert for Whole-Body PET Scanners. IEEE Transactions on Nuclear Science, Jun. 2006. 53(3): p. 1143-1148.

Tai, Yuan-Chuan., et al., Virtual-pinhole PET. J Nucl Med, 2008. 49(3): p. 471-479.

Wu, Heyu, et al., Micro Insert: A Prototype Full-Ring PET Device for Improving the Image Resolution of a Small-Animal PET scanner. J. Nucl Med, Oct. 2008. 49(10): p. 1668-1676.

Zhou, J. et al., Adaptive Imaging for Lesion Detection Using a Zoom-in PET System. IEEE Trans Med Imaging, 2011. 30(1): p. 119-130.

Studen, A., et al., A silicon PET probe. Nuclear Instruments & Methods in Physics Research Section a—Accelerators Spectrometers Detectors and Associated Equipment, 2011. 648: p. S255-S258.

Clinthorne, N., et al., A High-Resolution PET Demonstrator using a Silicon "Magnifying Glass". Physics Procedia, 2012. 37: p. 1488-1496.

Brzezinski, K., et al., Study of a high-resolution PET system using a silicon detector probe. Physics in Medicine and Biology, 2014. 59(20): p. 6117-6140.

Park, Sang-June, et al., Performance evaluation of a very high resolution small animal PET imager using silicon scatter detectors. Physics in Medicine and Biology, Jun. 2007. 52(10): p. 2807-2826.

Park, Sang-June, et al., Design of a very high-resolution small animal PET scanner using a silicon scatter detector insert. Physics in Medicine and Biology, Sep. 2007. 52(15): p. 4653-4677.

Eo, J.S., et al., Imaging sensitivity of dedicated positron emission mammography in relation to tumor size. The Breast, 2012. 21(1): p. 66-71.

Keesing, D.B., et al., Image reconstruction and system modeling techniques for virtual-pinhole PET insert systems. Physics in Medicine and Biology, 2012. 57(9): p. 2517-2538.

Mathews, A.J., et al., Improving PET imaging for breast cancer using Virtual Pinhole PET half-ring insert. Physics in Medicine and Biology, 2013. 58(18): p. 6407-6427.

\* cited by examiner

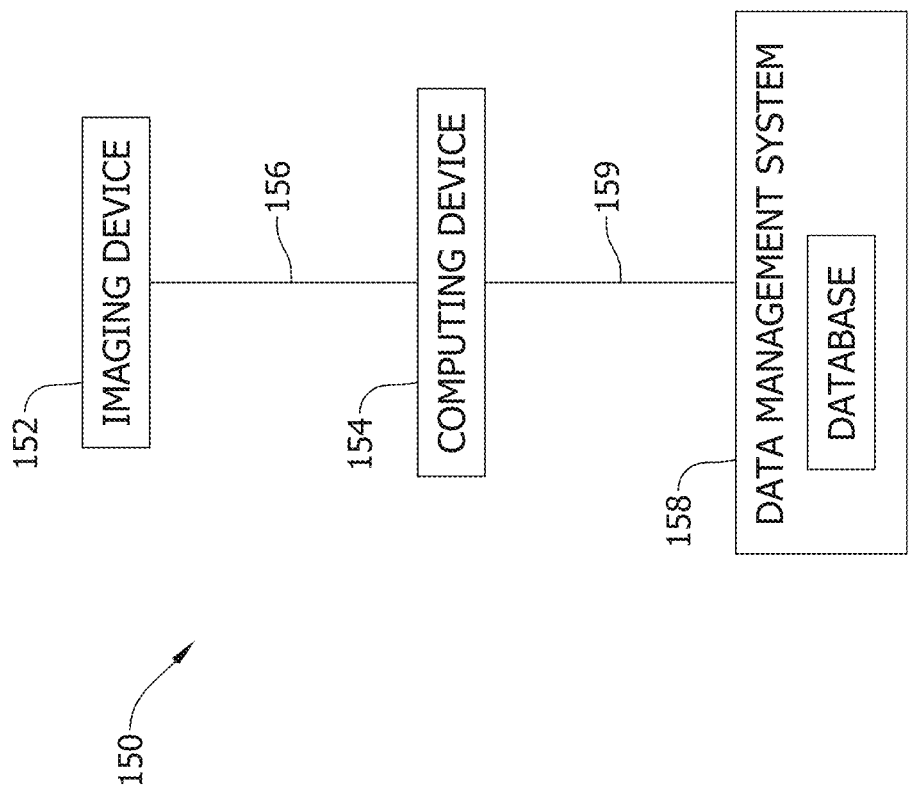

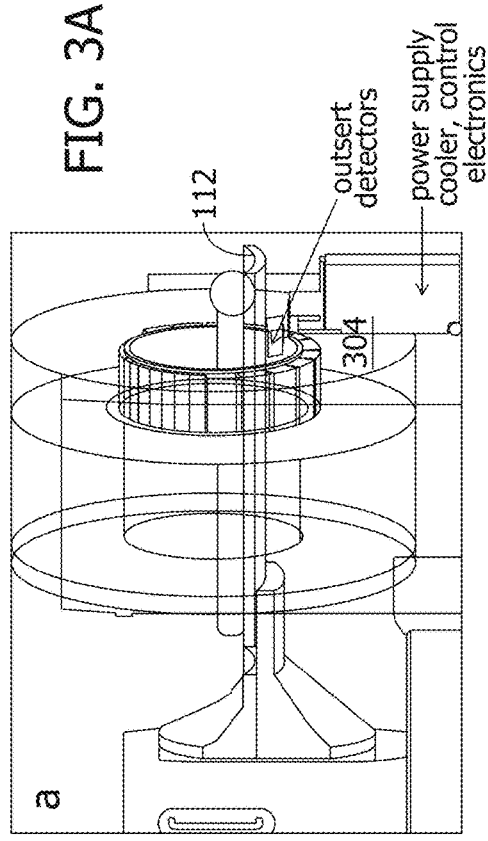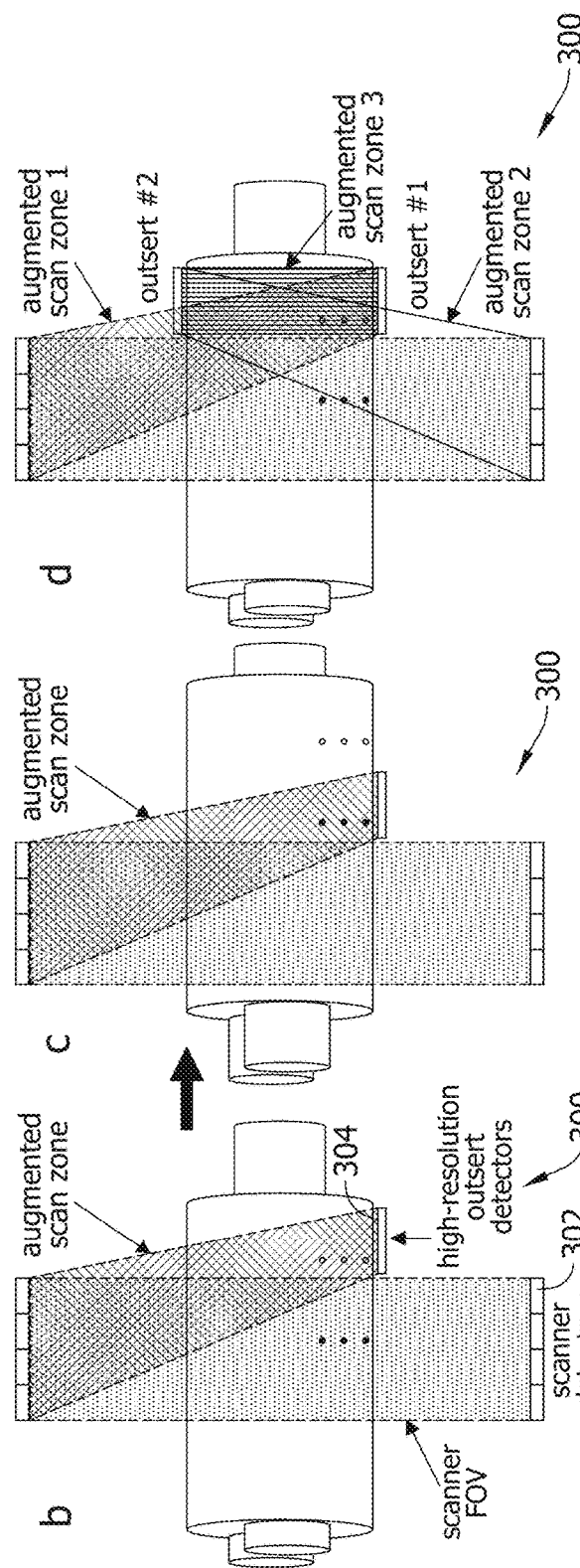

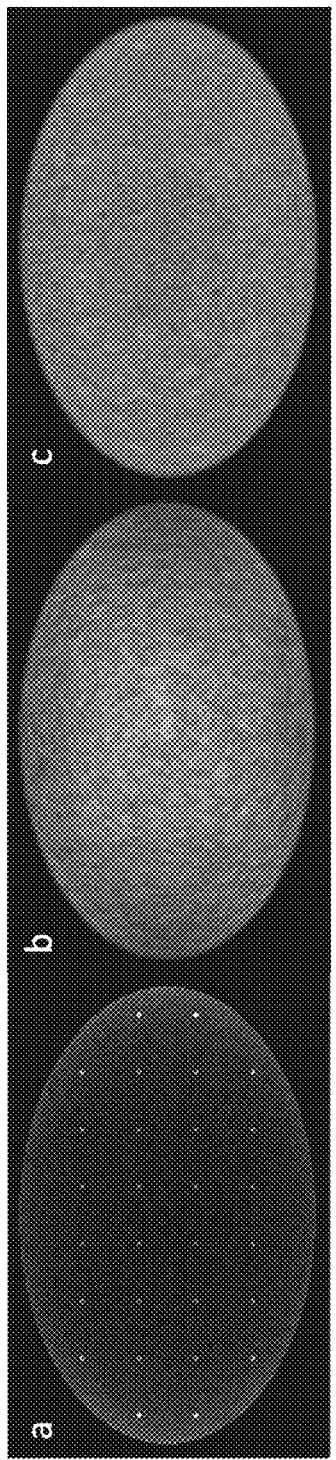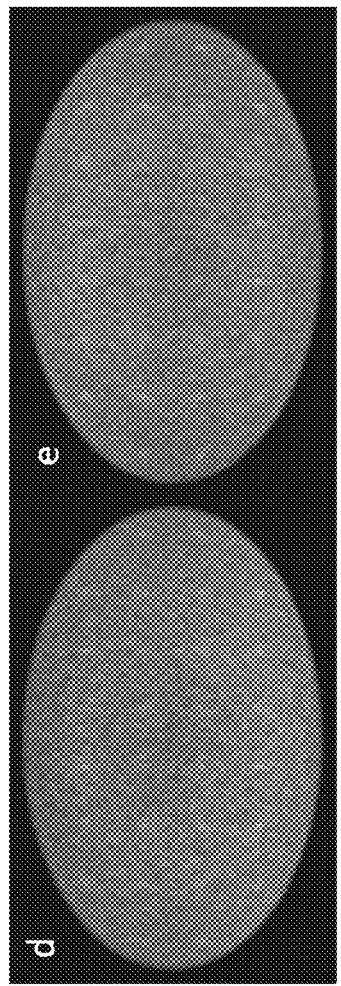
FIG. 7A  Decay map of detected events
FIG. 7B  Biograph 40
FIG. 7C  Biograph Vision
FIG. 7D  Biograph Vision + 1 Outsert
FIG. 7E  Biograph Vision + 2 Outserts

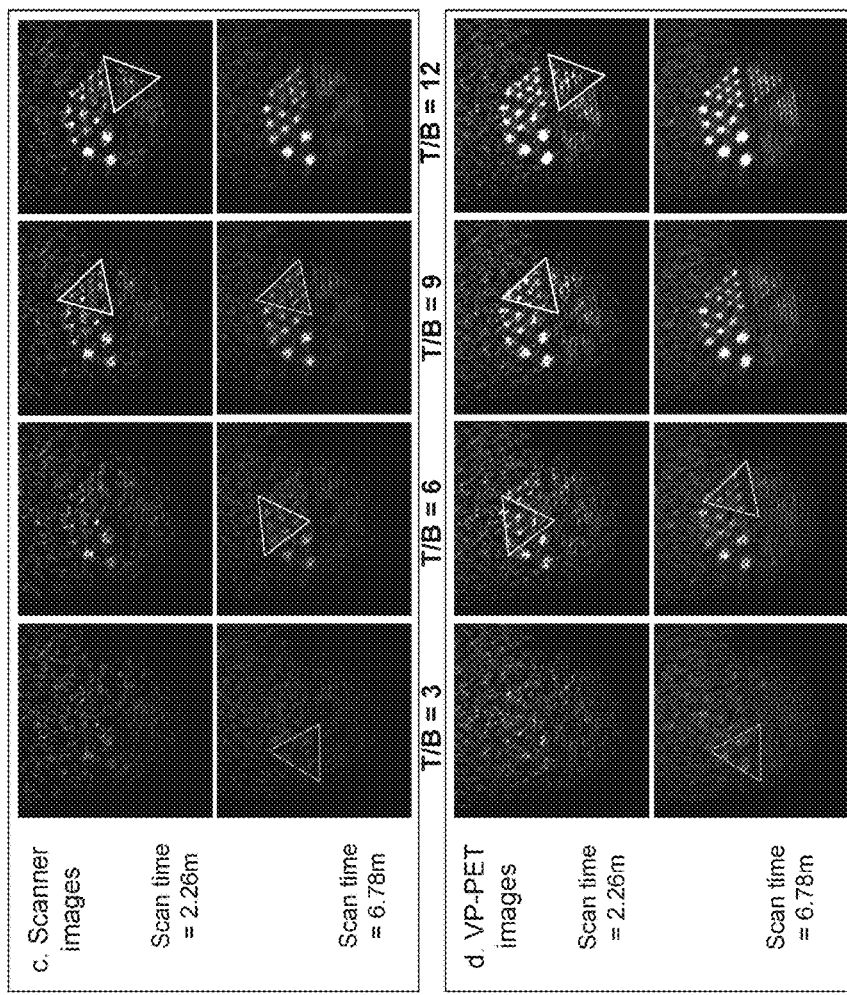
FIG. 9C
FIG. 9D
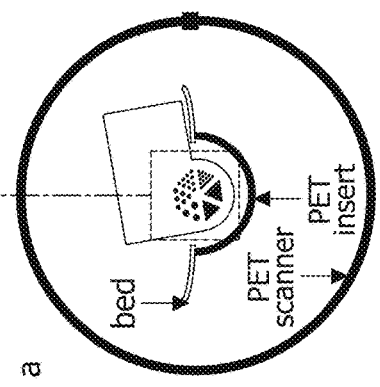
FIG. 9A
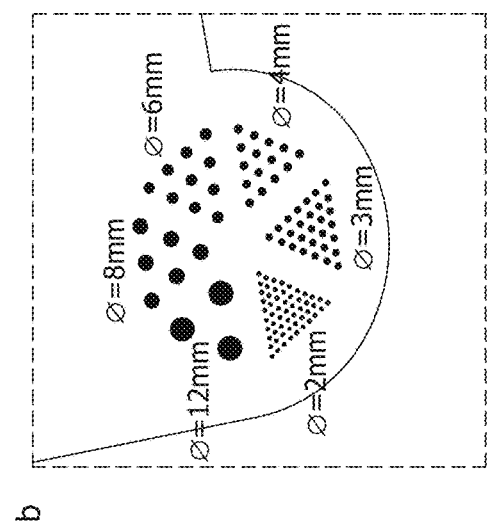
FIG. 9B

Schema of human study

METHODS AND APPARATUS FOR IMPROVING THE IMAGE RESOLUTION AND SENSITIVITY OF WHOLE-BODY POSITRON EMISSION TOMOGRAPHY (PET) IMAGING

CROSS-REFERENCE TO RELATED APPLICATION

This application claims the benefit of U.S. Provisional Application Ser. No. 62/773,595, filed Nov. 30, 2018, entitled "Methods and Apparatus for Improving the Image Resolution and Sensitivity of Whole-Body PET Imaging," which is hereby incorporated herein by reference in its entirety.

GOVERNMENTAL SUPPORT

This invention was made with government support under grant number RO1 CA136554 awarded by National Institutes of Health. The government has certain rights in the invention.

BACKGROUND

The field of the disclosure relates generally to imaging systems and methods, and more particularly to systems and methods for improving image resolution and sensitivity of a whole body positron emission tomography (PET) system by including one or more detector panel in addition to the detector array of the PET system.

Cancer continues to be a leading cause of death in the US and worldwide. Patients with early stage cancer are treated with surgery and patients with advanced stage disease or lymph node metastases are treated with chemotherapy or radiation therapy. Surgery is the preferred treatment for early stage disease because it is curative. If patients undergo surgery and are found to have metastatic cancer, the patients will require additional chemotherapy or radiation therapy post-operatively. A treatment of combining surgery and post-operative chemo- or radiation-therapy incurs much greater morbidity than treatment with either treatment alone. Therefore, accurate staging of the disease is crucial for the treatment planning and disease management for cancer patients.

To guide therapy choice, pre-treatment imaging is obtained with combinations of computed tomography (CT), positron emission tomography/CT (PET/CT), or magnetic resonance imaging (MRI). Fluorodeoxyglucose-PET (FDG-PET) generally outperforms CT and MRI for metastatic cancer detection. Unfortunately, the sensitivity of PET/CT imaging for detection of lymph node metastasis may decrease significantly in early stage disease. For example, the sensitivity of PET/CT for detecting pelvic lymph node metastases is only approximately 50% in patients with stages Ib to IIa diseases in cervical cancer patients. That is, approximately one-half of patients in this population with positive pelvic lymph nodes will be under-staged and undergo needless surgery resulting in increased rates of severe toxicity by receiving both surgery and post-operative chemo-radiation. Accordingly, there is an unmet clinical need for technologies that improve the detection of metastatic lymph nodes in order to decrease unnecessary morbidity and improve patient management.

Combined PET and CT is a proven technique for the detection of primary and metastatic cancers. It is used clinically for staging, restaging, and monitoring of treatment response of many types of cancers. The detection of lesions of unknown location is typically done by a whole-body imaging protocol scanning a patient from the skull apex to upper thighs in multiple bed positions. The actual scan duration is often limited to 2-3 minutes per position due to factors such as a patient's ability to remain still, an amount of attenuation by patient's body mass, clinical throughput, and the cost-benefit ratio of extended imaging time. With such short scan duration, the quality of whole-body PET images is often limited by counting statistics rather than the intrinsic spatial resolution of a scanner. Therefore, there is a need of systems and methods that enhance the signal-to-noise ratio of images (e.g., time-of-flight (TOF) PET) with increased counting statistics.

BRIEF DESCRIPTION

In one aspect, a positron emission tomography (PET) system of imaging a target region of a subject is provided. The system includes a detector array and a detector panel. The detector array includes an array of gamma ray detectors defining a field of view and configured to detect at least one coincidence event. The detector panel includes an array of gamma ray detectors having higher resolutions than the detector array and positioned in closer proximity to a patient table than the detector array. The detector panel is positioned outside the field of view defined by the detector array during at least a portion of scanning by the PET system. The detector panel is configured to detect at least one coincidence event in cooperation with the detector array. The control unit is configured to be in communication with the detector panel and the detector array, and configured to control the detector array and the detector panel to operate in cooperation with each other.

In another aspect, a device to enhance an image resolution of a PET system is provided. The PET system is configured to image a target region of a subject. The device includes a detector panel including an array of gamma ray detectors having higher resolutions than a detector array of the PET system and positioned in closer proximity to a patient table than the detector array. The detector panel is positioned outside a field of view defined by the detector array during at least a portion of scanning by the PET system and configured to detect at least one coincidence event in cooperation with the detector array. The detector panel is configured to be in communication with a control unit of the PET system, the control unit configured to be in communication also with the detector array and configured to control the detector array and the detector panel to operate in cooperation with each other.

In yet another aspect, a method for enhancing a resolution of an image of a target region within a subject obtained using a PET system is provided. The PET system includes a detector array including an array of gamma ray detectors that define a field of view and configured to detect at least one coincidence event and a control unit configured to be in communication with the detector array and configured to control the detector array. The method includes providing a detector panel including an array of gamma ray detectors having higher resolutions than the detector array, the detector panel configured to be positioned in closer proximity to a patient table than the detector array and positioned outside the field of view defined by the detector array during at least a portion of scanning by the PET system. The detector panel is configured to detect at least one coincidence event in cooperation with the detector array, and the control unit configured to be in communication also with the detector panel and configured to control the detector array and the detector panel to operate in cooperation with each other.

BRIEF DESCRIPTION OF THE DRAWINGS

The drawings described below illustrate various aspects of the disclosure.

FIG. 1B is a block diagram of an example imaging system using the PET system shown in FIG. 1A.

FIG. 3A is a schematic diagram of an example of augmented whole-body scanning via magnifying PET (AWSM-PET) scanner system that includes an example outsert.

FIG. 3B is an illustration of fields of view (FOVs) of the scanner detectors and of detectors of the outsert shown in FIG. 3A.

FIG. 3C is an illustration of the FOVs of the scanner detectors and the detectors of the outsert shown in FIG. 3A after the patient table and a patient's body have been moved along the axial direction of the scanner.

FIG. 3D is an illustration of the scanner system shown in FIG. 3A including two outserts and the FOVs covered by their detectors.

FIG. 7A is an illustration of a decay map of detected coincidence events from a body phantom.

FIG. 7B is an image of the phantom shown in FIG. 7A that is acquired by a Biograph 40™ PET scanner.

FIG. 7C is an image of the phantom shown in FIG. 7A that is acquired by a Biograph Vision™ PET scanner.

FIG. 7D is an image of the phantom shown in FIG. 7A that is acquired by a Biograph Vision™ PET scanner including one outsert.

FIG. 7E is an image of the phantom shown in FIG. 7A that is acquired by a Biograph Vision™ PET scanner including two outserts.

FIG. 9A is an illustration of geometry of a Monte Carlo simulation study using a VP magnifying PET insert for a simulated breast and body imaging.

FIG. 9B is a magnified view of the section of the simulated breast region as marked in FIG. 9A.

FIG. 9C are images acquired by the scanner detectors.

FIG. 9D shows images acquired by a VP-PET scanner.

DETAILED DESCRIPTION

Figure 1A:
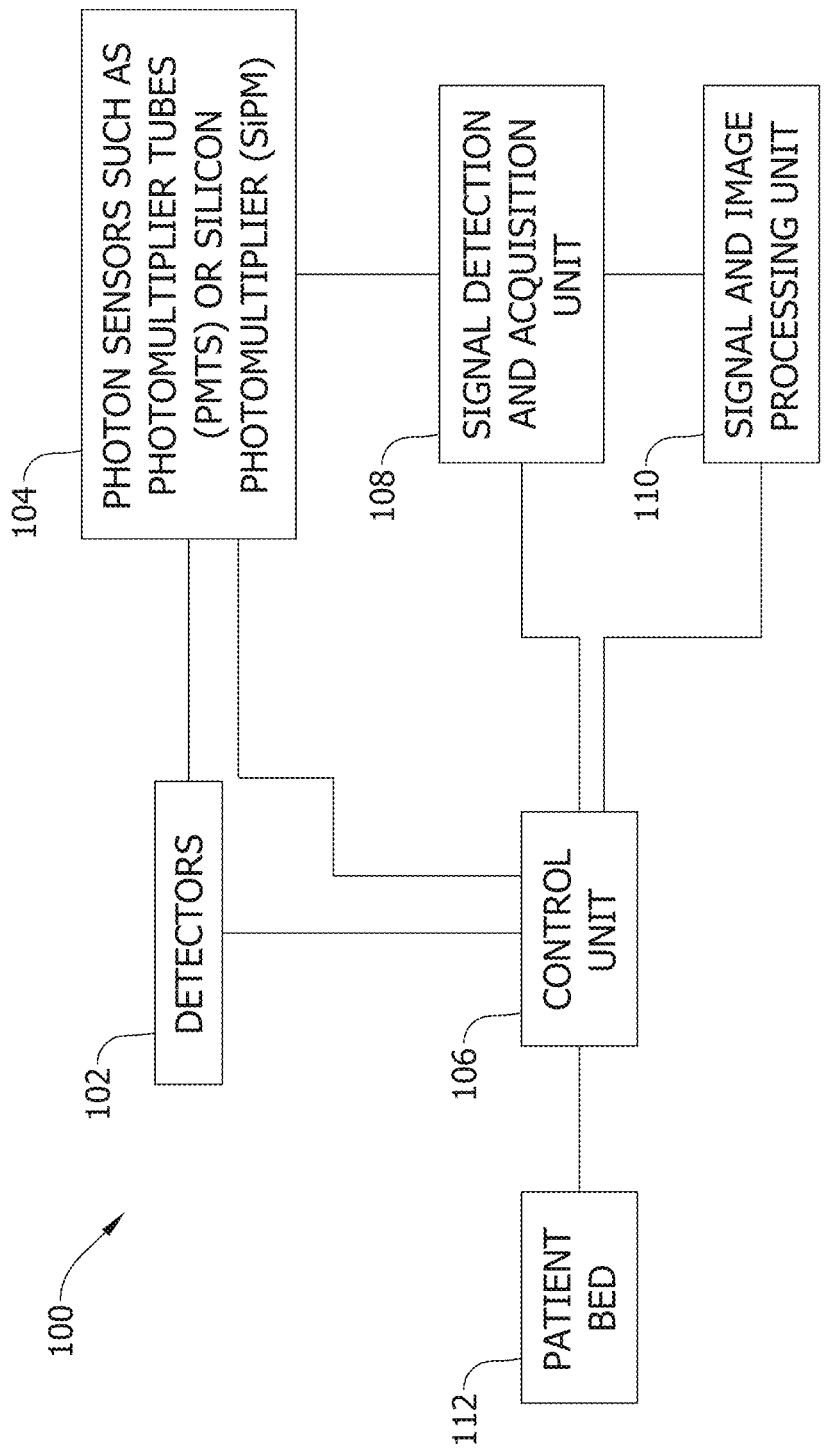
FIG. 1A is a block diagram of an example positron emission tomography (PET) system.

The systems and methods described herein relate to imaging systems and methods, and more specifically, systems and methods of a positron emission tomography (PET) system having a detector panel of high-resolution gamma-ray detectors positioned in closer proximity to a patient table than the detector array of the scanner detectors for imaging a subject. As used herein, a subject may be a human or an animal, or part of a human or an animal. With the detector panel, the signal-to-noise ratio of the PET is increased.

The suboptimal performance of whole-body Fluorodeoxyglucose (FDG) PET/computed tomography (PET/CT) for detecting small lesions is partially due to the limited counting statistics of the data and partially due to the limited spatial resolution of clinical scanners. To find distant metastasis at unknown location(s), a patient is scanned from the base of skull to thighs in multiple steps, typically using 2-3 minutes per bed position non-discriminatorily. With this short scan duration, the statistical uncertainty increases the difficulty for an already challenging task of delineating a small uptake in a limited number of cancerous cells from overwhelming background noise due to non-specific uptakes in surrounding tissue and blood. To accommodate a patient's body, clinical PET scanners include large rings of γ-ray detectors with a ring diameter typically greater than 80 cm. The image resolution of PET is known to be limited by positron range, photon acolinearity and detector intrinsic spatial resolution. A large ring diameter limits the image resolution of a whole-body PET scanner to be no better than approximately 2 mm full-width-at-half-maximum (FWHM) by the photon acolinearity effect, where the two γ rays from a positron annihilation are not emitted along a straight line. This resolution limit of PET precludes γ-ray detectors having further increased resolution in a whole-body scanner design because the higher-cost detectors do not significantly improve the overall image resolution.

The systems and methods disclosed herein include a detector panel having high-resolution gamma-ray detectors in addition to scanner detectors to increase the signal-to-noise ratio of a PET system. The high-resolution detectors have higher resolutions than the detector array of the scanner detectors and are positioned in closer proximity to a patient table than the detector array.

In some embodiments, an augmented whole-body scanning via magnifying PET (AWSM-PET) system is used. A detector panel of high-resolution detectors is positioned outside of the field of view (FOV) covered by the scanner detectors such that the detector panel detects incidents outside the FOV of the scanner detectors.

In some embodiment, a targeted virtual-pinhole PET (TVP-PET) system is used. A detector panel of high-resolution detectors is positioned in close proximity of a target region in a subject and follows the target region as the patient table moves during a PET scanning. As a result, the system provides increased incident detection of the target region. A target region may be anatomy in a patient in which a physician is interested, such as a cervix of a subject.

FIG. 1A is a block diagram of an example PET system 100. System 100 includes detectors 102 having a plurality of scintillators, photomultiplier tubes (PMTs) or silicon photomultipliers (SiPM) 104, a control unit 106, a signal detection and acquisition unit 108, a signal and image processing unit 110, and a patient bed unit 112. Scintillators of detectors 102 include scintillation materials such as cerium-doped lutetium oxyorthosilicate (LSO) that convert γ-rays emitted from a subject to photons. Two photons are observed at roughly at the same time (in coincidence) in a detector ring. An annihilation event, i.e., the radioactive tracer, can be located somewhere on the line connecting the two photon-detection points. The detected photons are therefore called coincidence events and used to reconstruct an image of the radioactive tracer that reflects the function of the anatomy of the subject at the location of the radioactive tracer. During scanning or detection of coincidence events by system 100, detectors 102 scan around a subject. PMTs or SiPM 104 convert the photons to electrical signals, which are then acquired, processed, and converted to digital signals through signal detection and acquisition unit 108. Images of the subject are generated based on the outputted digital signals using signal and image processing unit 110. To image a section of a patient's body that is longer than the scanner's imaging field-of-view, control unit 106 may control patient bed 112 to move a patient through the scanner's imaging field-of-view either continuously or step-by-step while the coincidence events are collected. Control unit 106 is in communication with and controls detectors 102, PMTs or SiPM 104, signal detection and acquisition unit 108, signal and image processing unit 110, and patient bed 112 such that system 100 detects coincidence events and reconstruct an image based on the coincidence events.

FIG. 1B is a block diagram of an example imaging system 150 using an imaging device 152. Imaging device may be PET system 100 shown in FIG. 1A, a PET/CT system, or a PET/magnetic resonance imaging (PET/MRI) system. System 150 further includes a computing device 154 to receive imaging data from the imaging device 152. Computing device 154 may be configured to control the imaging device 152.

System 150 further includes a data management system 158 that is coupled to computing device 154 via a network 159. In some embodiment, the computing device 154 includes a data management system 158. Data management system 158 may be any device capable of accessing network 159 including, without limitation, a desktop computer, a laptop computer, or other web-based connectable equipment. More specifically, in the example embodiment, data management system 158 includes a database 160 that includes previously acquired data of other subjects. In the example embodiment, database 160 can be fully or partially implemented in a cloud computing environment such that data from the database is received from one or more computers (not shown) within system 150 or remote from system 150. In the example embodiment, the previously acquired data of the other subjects may include, for example, a plurality of measurements of lesion region of other subjects. The information about lesion location from other subjects who have similar diseases can be used to direct the scanning of patients using the systems and methods described herein. Database 160 can also include any additional information of each of the subjects that enables system 150 to function as described herein.

In the example embodiment, in system 150, computing device 154 is coupled to imaging device 152 via a data conduit 156. It should be noted that, as used herein, the term "couple" is not limited to a direct mechanical, electrical, and/or communication connection between components, but may also include an indirect mechanical, electrical, and/or communication connection between multiple components. Imaging device 152 may communicate with computing device 154 using a wired network connection (e.g., Ethernet or an optical fiber), a wireless communication means, such as radio frequency (RF), e.g., FM radio and/or digital audio broadcasting, an Institute of Electrical and Electronics Engineers (IEEE®) 802.11 standard (e.g., 802.11(g) or 802.11(n)), the Worldwide Interoperability for Microwave Access (WIMAX®) standard, a short-range wireless communication channel such as BLUETOOTH®, a cellular phone technology (e.g., the Global Standard for Mobile communication (GSM)), a satellite communication link, and/or any other suitable communication means. IEEE is a registered trademark of the Institute of Electrical and Electronics Engineers, Inc., of New York, N.Y. WIMAX is a registered trademark of WiMax Forum, of Beaverton, Oreg. BLUETOOTH is a registered trademark of Bluetooth SIG, Inc. of Kirkland, Wash.

In various embodiments, data management system 158 communicates with computing device 154 using a wired network connection (e.g., Ethernet or an optical fiber), a wireless communication means, such as, but not limited to radio frequency (RF), e.g., FM radio and/or digital audio broadcasting, an Institute of Electrical and Electronics Engineers (IEEE®) 802.11 standard (e.g., 802.11(g) or 802.11(n)), the Worldwide Interoperability for Microwave Access (WIMAX®) standard, a cellular phone technology (e.g., the Global Standard for Mobile communication (GSM)), a satellite communication link, and/or any other suitable communication means. More specifically, in the example embodiment, data management system 158 transmits the data for the subjects to computing device 154. While the data is shown as being stored in database 160 within data management system 158, it should be noted that the data of the subjects may be stored in another system and/or device. For example, computing device 154 may store the data therein.

Figure 2:
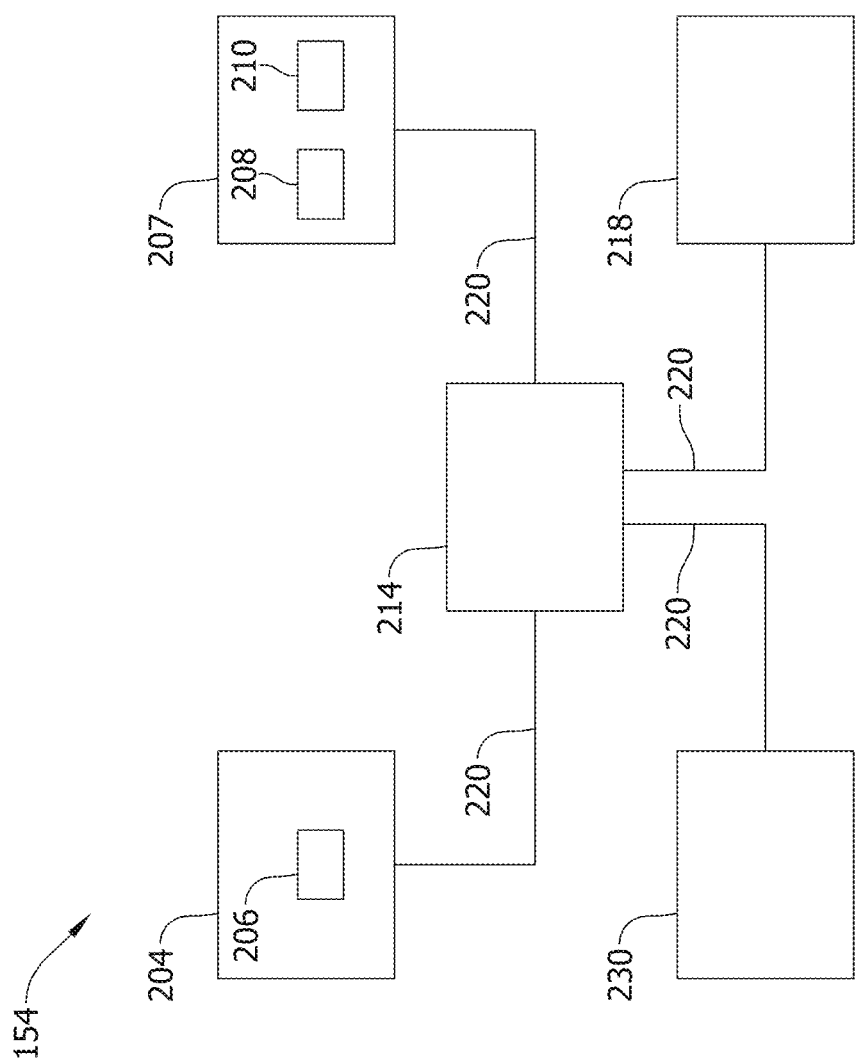
FIG. 2 is a block diagram of an example computing device.

FIG. 2 is a block diagram of computing device 154 such as control unit 106. In the example embodiment, computing device 154 includes a user interface 204 that receives at least one input from a user, such as an operator of imaging device 152 or system 150. User interface 204 may include a keyboard 206 that enables the user to input pertinent information. Additionally or alternatively, user interface 204 may include, for example, a pointing device, a mouse, a stylus, a touch sensitive panel (e.g., a touch pad or a touch screen), a gyroscope, an accelerometer, a position detector, and/or an audio input interface (e.g., including a microphone).

Moreover, in the example embodiment, computing device 154 includes a presentation interface 207 that presents information, such as input events and/or validation results, to the user. Presentation interface 207 may include a display adapter 208 that is coupled to at least one display device 210. More specifically, in the example embodiment, display device 210 may be a visual display device, such as a cathode ray tube (CRT), a liquid crystal display (LCD), a light emitting diode (LED) display, an organic LED (OLED) display, and/or an "electronic ink" display. Alternatively, presentation interface 207 may include an audio output device (e.g., an audio adapter and/or a speaker) and/or a printer.

Computing device 154 also includes a processor 214 and a memory device 218. Processor 214 is coupled to user interface 204, presentation interface 207, and to memory device 218 via a system bus 220. In the example embodiment, processor 214 communicates with the user, such as by prompting the user via presentation interface 207 and/or by receiving user inputs via user interface 204. The term "processor" refers generally to any programmable system including systems and microcontrollers, reduced instruction set circuits (RISC), application specific integrated circuits (ASIC), programmable logic circuits (PLC), and any other circuit or processor capable of executing the functions described herein. The above examples are exemplary only, and thus are not intended to limit in any way the definition and/or meaning of the term "processor."

In the example embodiment, memory device 218 includes one or more devices that enable information, such as executable instructions and/or other data, to be stored and retrieved. Moreover, memory device 218 includes one or more computer readable media, such as, without limitation, dynamic random access memory (DRAM), static random access memory (SRAM), a solid state disk, and/or a hard disk. In the example embodiment, memory device 218 stores, without limitation, application source code, application object code, configuration data, additional input events, application states, assertion statements, validation results, and/or any other type of data. Computing device 154, in the example embodiment, may also include a communication interface 230 that is coupled to processor 214 via system bus 220. Moreover, communication interface 230 is communicatively coupled to imaging device 152 and data management system 158.

In the example embodiment, processor 214 may be programmed by encoding an operation using one or more executable instructions and providing the executable instructions in memory device 218. In the example embodiment, processor 214 is programmed to select a plurality of measurements that are received from imaging device 152. The plurality of measurements may include, for example, a plurality of voxels of at least one image of the subject, wherein the image may be generated by processor 214 within computing device 154. The image may also be generated by an imaging device (not shown) that may be coupled to computing device 154 and imaging device 152, wherein the imaging device may generate the image based on the data received from imaging device 152 and then the imaging device may transmit the image to computing device 154 for storage within memory device 218. Alternatively, the plurality of measurements may include any other type measurement of the lesion region that enables system 150 to function as described herein.

Although, in some of the examples provided below, the systems and methods disclosed herein are used on certain part of the body or certain types of lesions, the systems and methods are not limited to that part of human or animal body or that type of lesions. Further, method aspects will be in part apparent and in part explicitly discussed in the following description.

EXAMPLES

Example 1

Augmented Whole-Body Scanning Via Magnifying PET (AWSM-PET)

FIGS. 3A-3D are illustrations of an example system 300 including the AWSM-PET technology. System 300 is a whole-body PET scanner augmented with or including additional detectors besides detectors of the whole-body scanner to increase the resolution and sensitivity of the system. In the exemplary embodiment, system 300 includes a detector array 302 of the scanner and a detector panel 304 additional to scanner detectors 302. Detector array 302 includes an array of gamma-ray detectors configured to detect at least one coincidence event. Detector panel 304 includes an array of high-resolution gamma ray detectors positioned in closer proximity to a patient table 112 relative to detector array 302. FIG. 3A is schematic diagram of a prototype AWSM-PET device integrated with a Siemens Biograph Vision™ PET/CT scanner. A group of high-resolution PET detectors are placed close to a patient's body but outside the scanner's imaging FOV in the axial direction. These added-on detectors are sometimes referred to herein as "outsert" in contrast to an "insert" where high-resolution detectors are placed inside a scanner's imaging FOV. That is, during the entire scanning by system 300, detector panel 304 is positioned outside the FOV of detector array 302. Being outside of the scanner, the presence of these outsert detectors does not interfere with the operation of the native scanner. Therefore, standard whole-body PET/CT images can still be acquired independent of the add-on AWSM-PET device. FIGS. 3B and 3C show a group of high-resolution "outsert" detectors are placed outside of the scanner's axial FOV. Coincidence detection between the outsert detectors and scanner detectors creates an augmented scan zone that collects additional events simultaneously when a patient undergoes a whole-body scan. A section of the body is first scanned by the scanner's native FOV (in gray) and then by the augmented imaging FOV (in blue) when a patient is moved from one bed position (FIG. 3B) to the next position (3C). FIG. 3D shows a dual-panel AWSM-PET device that generates 2 additional augmented scan zones 2 and 3, besides scan zone 1 with a single additional panel to further improve the overall resolution and sensitivity.

Establishing coincidence detection between the outsert detectors and the scanner detectors permits the system to detect additional coincidence events that are otherwise missed by the native scanner. For example, without an outsert, annihilation γ rays originated from the patient's body in the blue zone (augmented scan zone marked in FIG. 3B) may be undetected by the scanner if one of the two γ rays travels outwards and hit the outsert detectors. These extra coincidence events, when augmented to the native scanner data for joint image reconstruction, increase the overall counting statistics and therefore improve the noise characteristics of the PET images. Further, the outsert's high-resolution detectors are placed close to a patient's body for zoom-in imaging using a virtual-pinhole PET geometry. The image resolution of the native scanner can be improved when the higher-resolution events are added to jointly reconstruct PET images. This is an extension and new application of the virtual-pinhole PET insert technology that we previously developed and validated, as will be described below. As a patient's body is moved across the scanner's imaging FOV during a whole-body imaging session, the patient is also being scanned by the AWSM-PET device simultaneously. An optimized imaging protocol and accurate image reconstruction algorithm allows AWSM-PET technology to enhance the performance of a PET scanner without increasing scan time for whole-body cancer imaging.

1.1. Prior Prototype Virtual-Pinhole (VP) PET System

Figure 4B:
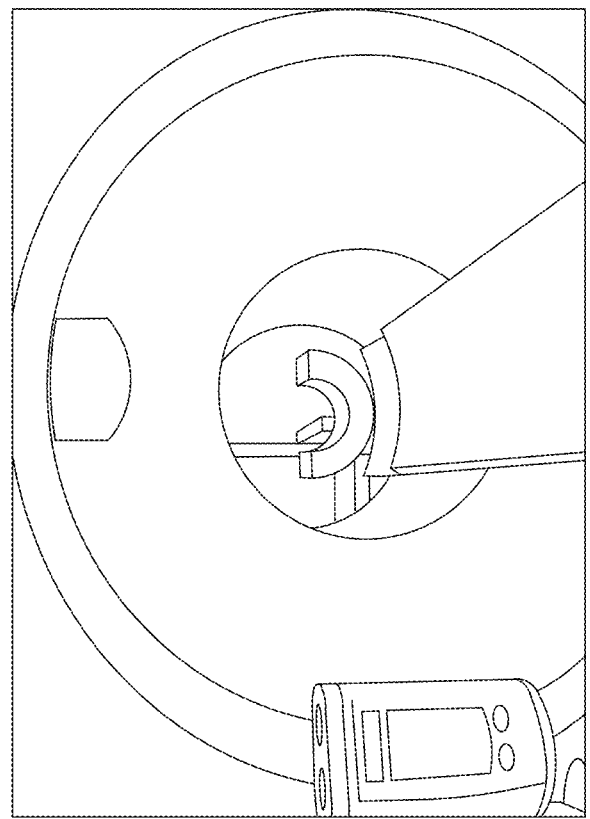
FIG. 4B is a front perspective view of the PET scanner shown in FIG. 4A.
Figure 4A:
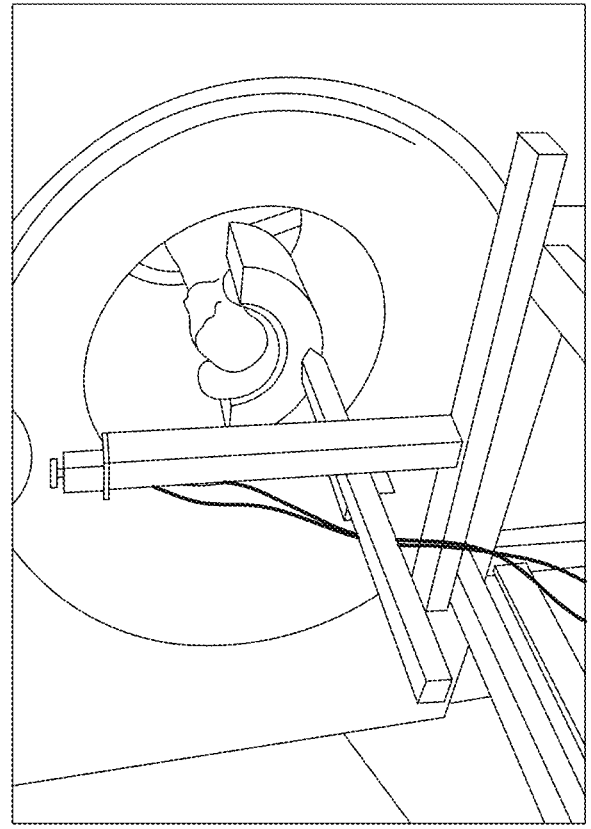
FIG. 4A is a rear perspective view of a PET scanner having virtual-pinhole magnifying PET (VP-PET) insert.

A proof-of-principle virtual-pinhole magnifying PET insert system (shown in FIGS. 4A and 4B) was previously built using 28 PET detector modules and arranged them to form two half rings. FIGS. 4A and 4B show front (FIG. 4A) and rear (FIG. 4B) views of a human PET/CT scanner integrated with the insert. Each detector module includes 13×13 lutetium oxyorthosilicate (LSO) crystals read out by a multi-anode PMT. The LSO crystals measure 2×2×5 mm each. The system was centered in the imaging FOV in a Siemens Biograph 40™ PET/CT scanner. One of the PET detector rings (out of a 4-ring system) was disabled and its associated electronics were used to process the VP-PET detector signal for coincidence detection. This integrated system has a transaxial FOV of approximately 24 cm in diameter and an axial FOV of 16.4 cm, with approximately 6 cm of the axial FOV in the center having higher resolution images.

Figure 5A:
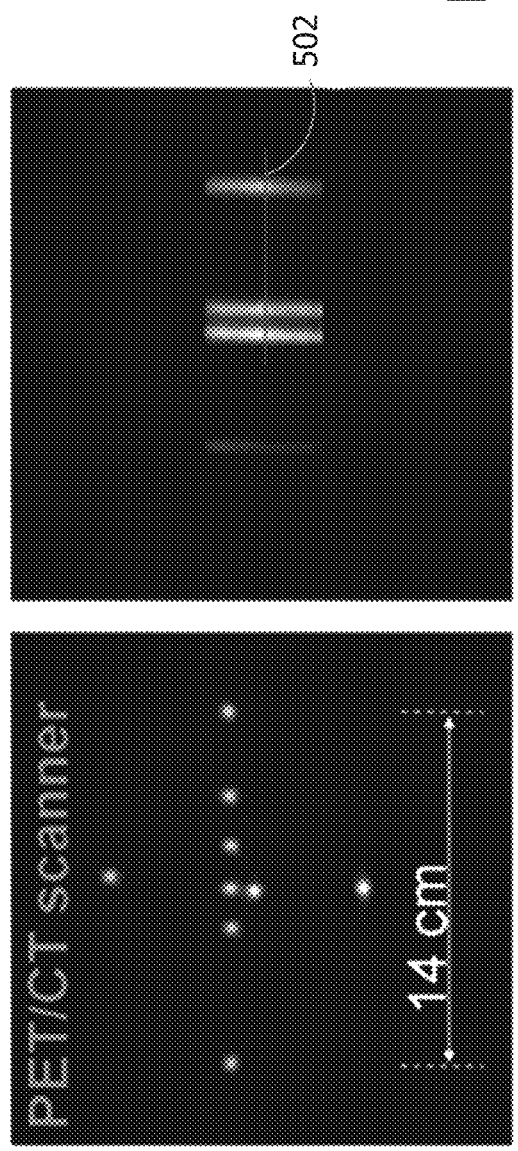
FIG. 5A is an illustration of images of $^{68}$Ge line sources acquired using scanner detectors of the PET scanner shown in FIGS. 4A-4B.
Figure 5B:
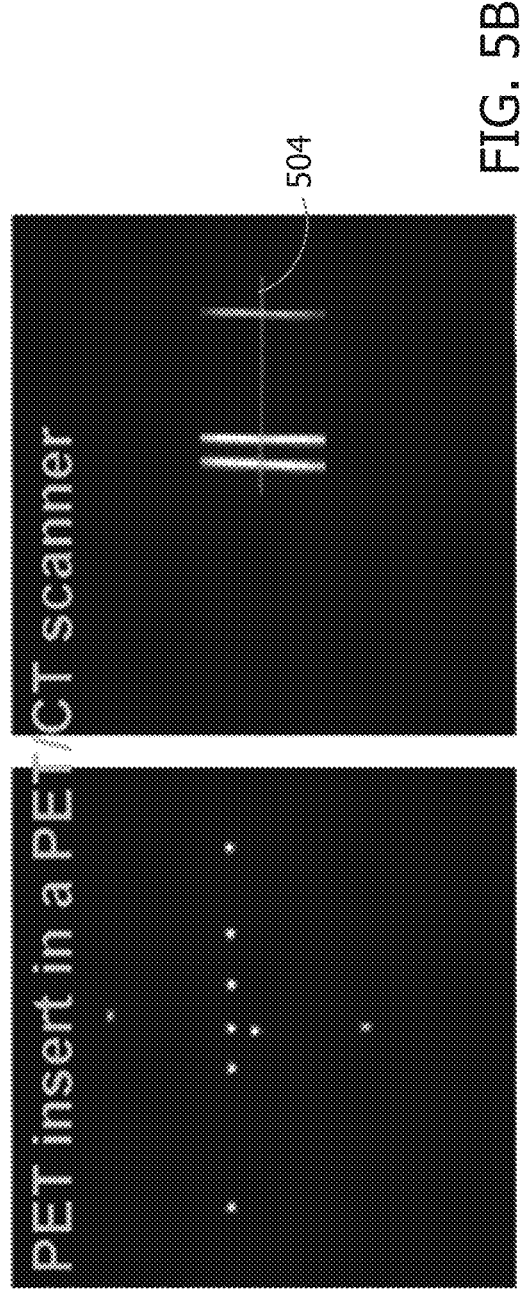
FIG. 5B is an illustration of images of $^{68}$Ge line sources acquired using scanner detectors of the PET scanner shown in FIG. 4A and the detectors of the VP-PET shown in FIG. 4A.
Figure 5C:
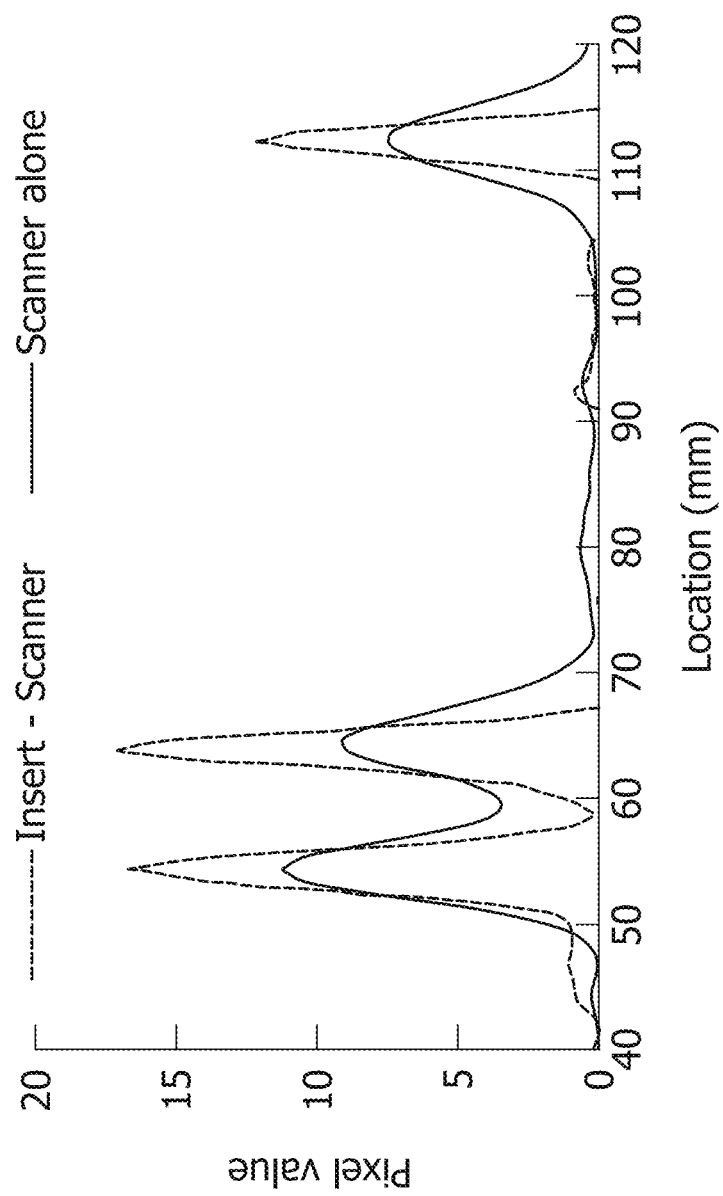
FIG. 5C is an illustration of profiles along lines in the images shown in FIGS. 5A and 5B.

The image resolution of the integrated system was evaluated using a sealed $^{68}$Ge line source placed at 9 different locations in the imaging FOV. $^{68}$Ge line source images from the scanner are shown in FIG. 5A, and images from the augmented system are shown in FIG. 5B. FIG. 5C shows profiles of the line source images along a line 502, 504 depicted in FIGS. 5A and 5B. The images are reconstructed using the filtered back-projection algorithm with a ramp filter and no smoothing. The resolution of the original PET scanner ranges from 4.3 to 5.5 mm FWHM after the source dimension was corrected and subtracted. This agrees well with the reported performance of the Biograph™ PET/CT scanner. The resolution of the integrated VP-PET insert system ranges from 2.4 to 3.0 mm FWHM. This agrees well with theoretical calculation using Equation (1) below, which predicts 2.3 mm FWHM at the center of FOV.

$$R_{img} \approx 1.25 \cdot \sqrt{R_{src}^2 + \left[0.0088 \cdot \frac{d_1 \cdot d_2}{(d_1 + d_2)}\right]^2 + \left[\frac{d_2 \cdot w_1 + d_1 \cdot w_2 +}{2 \cdot (d_1 + d_2)}\right]^2} \quad (1)$$

where $d_1$=123 mm and $d_2$=428 mm are the radii of the detector rings in the virtual-pinhole PET device and the scanner, respectively, and $w_1$=2 mm and $w_2$=4 mm are the width of the LSO crystals in the virtual-pinhole PET and scanner, respectively.

1.2. Estimated Performance of a Prototype AWSM-PET System

An example AWSM-PET technology was evaluated using a Siemens Biograph Vision™ scanner through Monte Carlo simulation method. Siemens Biograph Vision™ is a clinical PET/CT that includes a 128-slice CT and an 8-ring PET scanner to offer 25.6 cm axial FOV. The PET scanner includes a total of 608 block detectors each made of a LSO crystal array (10×10 elements of 3.2 mm pitches) and a silicon photo-multiplier (SiPM) array (8×8 elements of 4 mm pitches). The 608 detectors are divided into 19 groups of 32 detectors each. Each group of 32 block detectors are arranged to form an eight (axially) by four (transaxially) array and supported by a detector electronics assembly (DEA) that determines the position, energy and timing of each event. Qualified single events are packaged and transmitted to a Gantry Interface Module (GIM). The GIM compares the time stamps of events from all 19 DEAs to identify coincidence events. Valid coincidence events are packaged and transmitted to a host computer as a stream of list mode data.

Image resolution: The Siemens Biograph Vision™ scanner has an excellent intrinsic spatial resolution (from 3.2 mm pitched LSO crystals). Using the equation (1), and substituting $w_2$=3.2 mm for the Biograph Vision™ scanner, the image resolution of an AWSM-PET system is estimated to be slightly over 2.0 mm FWHM at best if 1.6 mm LSO crystals are used for two outsert detectors. In contrast, the native image resolution of the Biograph Vision™ scanner is estimated to be from approximately 3.2 mm to more than 4 mm FWHM. If 0.8 mm LSO crystals are used for a dual-panel AWSM-PET system, the image resolution of the system is estimated to be better than 2 mm FWHM for a significant portion of the imaging FOV. This will overcome the theoretical resolution limit of 2 mm FWHM for whole-body PET imaging and may improve the diagnostic accuracy of whole-body PET/CT image for the detection of small metastatic lesions. Thus, the outserts and the technique disclosed herein provide a unique and cost-effective upgrade option to enhance the performance of the current state-of-the-art clinical whole-body PET/CT scanners further.

Figures 6A, 6B:
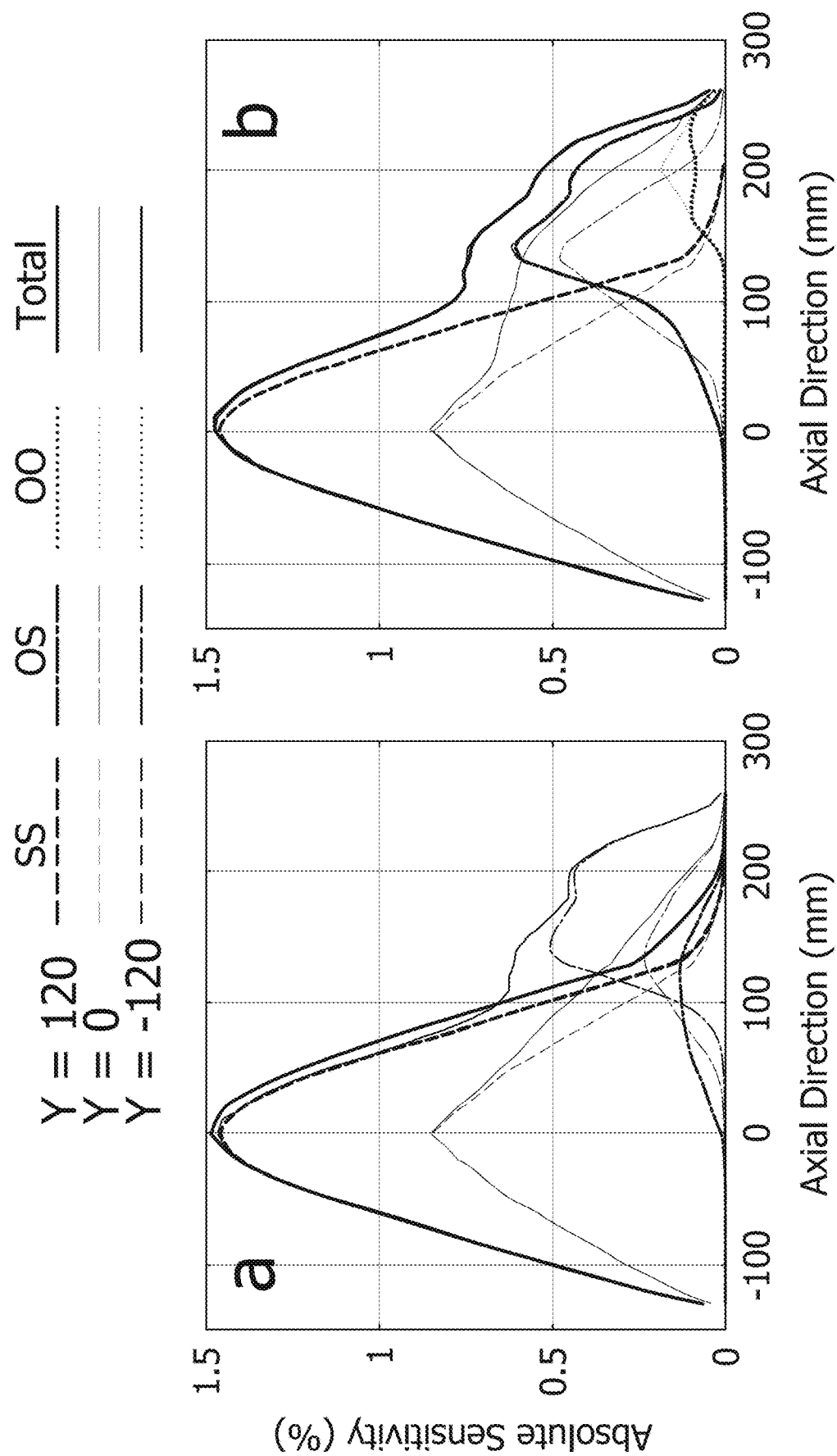
FIG. 6A is an illustration of sensitivity profiles of the scanner system shown in FIGS. 3A-3D with one outsert.
FIG. 6B is an illustration of sensitivity profiles of the scanner system shown in FIGS. 3A-3D with two outserts.

System sensitivity: The gain in system sensitivity is evaluated by simulating a Biograph Vision™ scanner with AWSM-PET technology using Monte Carlo technique. The AWSM-PET device includes either one or two outsert detectors. Each outsert detector was simulated as 32 block detectors, where each block detector was made of 40×40 LSO crystals each in the dimension of 0.8×0.8×7 mm. The timing resolution of the detectors was assumed to be 250 ps FWHM. For a single-panel AWSM-PET system, the outsert detector was positioned below the patient bed and directly outside of the PET scanner's axial FOV (same geometry as depicted in FIG. 3A). For a dual-panel AWSM-PET system, a second outsert detector was positioned above the patient. A $^{22}$Na point source was stepped across the scanner's imaging FOV along the axial direction at three different vertical positions (Y=−120 mm, 0, or 120 mm) from the center of FOV. FIGS. 6A and 6B show the sensitivity profiles of the simulated single-panel and dual-panel AWSM-PET systems, respectively. Coincidence events measured by the scanner (SS counts) or by the add-on detectors (OS counts) are shown in Table 1 below.

TABLE 1

| Biograph Vision ™ + 1 Outsert | | | |
|---|---|---|---|
| Y-coordinate | SS counts | OS counts | % gain |
| −120 mm | 1916024 | 464560 | 24.25% |
| 0 mm | 1064610 | 213004 | 20.01% |
| 120 mm | 1914747 | 143924 | 7.52% |
| Biograph Vision ™ + 2 Outserts | | | |
| Y-coordinate | SS counts | OS counts | OO counts | % gain |
| −120 mm | 1904817 | 583121 | 84291 | 35.04% |
| 0 mm | 1057855 | 393156 | 115330 | 48.07% |
| 120 mm | 1908202 | 582068 | 84129 | 34.91% |

The sensitivity gain of the scanner is computed from the number of coincidence events detected by the outsert detectors (outsert-to-scanner or OS counts, plus outsert-to-outsert or OO counts) divided by the number of events detected by the native scanner (SS counts), expressed in percentage. A scanner equipped with a dual-panel AWSM-PET device could gain up to 48% more counts than the native scanner for tissues near the center of the FOV. A scanner equipped with a single-panel AWSM-PET device would gain 7% to 24% more counts than the native scanner, with higher gain for tissues near the outsert detector.

The improvement in counting statistics by AWSM-PET technology is significant, especially with the dual-panel device. A native Biograph Vision™ scanner includes 19 DEA to support a total of 608 block detectors. An AWSM-PET device with two outsert detectors will require two external DEA and will increases the number of block detectors in the system by 10.5%. In return, the overall system sensitivity is increased by 35% to 48% for whole-body imaging applications. Therefore, the AWSM-PET technology is not only an innovative solution to improve the image resolution of a whole-body PET scanner, but also a cost-efficient strategy to improve the sensitivity of a scanner.

Contrast recovery and lesion detectability: To evaluate the benefits of the AWSM-PET technology for whole-body imaging, PET scanners were simulated with the following configurations. The object being imaged is a torso phantom with small lesions (4 mm in diameter) of low contrast (tumor to background activity concentration ratio (T/B)=4). Lesions that are hard to detect by current clinical scanners are purposely chosen. The activity concentration in the background is 5.3 kBq/mL assuming 10 mCi FDG is uniformly distributed in a 70 kg body. The acquisition time is 3 minutes per position using a step size of 15 cm for whole-body imaging. FIG. 7A shows the map of origins of coincidence events detected by the scanners, where few counts originated deep inside a body can escape and be detected. This illustrates the challenge of detecting small lesions deep in a body.

Four following scanner configurations were simulated: Siemens Biograph 40™ (4 mm LSO crystals, no time-of-flight PET (TOF-PET) capability), Biograph Vision™ (3.2 mm LSO crystals, TOF-PET with <250 ps CRT), Biograph Vision™ plus a single-panel AWSM-PET device (i.e., an outsert), and Biograph Vision™ plus a dual-panel AWSM-PET device (e.g., two outserts). The location and composition of the outsert detectors are identical to those used to simulate the system sensitivity in FIGS. 6A and 6B. The images were reconstructed with 1 mm$^3$ voxel size using a list-mode image reconstruction program. No regularization was applied during the reconstruction. A post-reconstruction smoothing with a 3-point averaging (along all three dimensions) was applied to the images before data analysis.

Results in FIG. 7B show that none of the lesions is detectable by the Biograph 40™, which has no TOF-PET feature and uses 4 mm LSO detectors. FIG. 7C shows that a few lesions that are close to the body surface may be detectable by the Biograph Vision™, although still with little confidence. FIGS. 7D and 7E show that more lesions become detectable when an AWSM-PET device is augmented to the Biograph Vision™ scanner.

Figure 8:
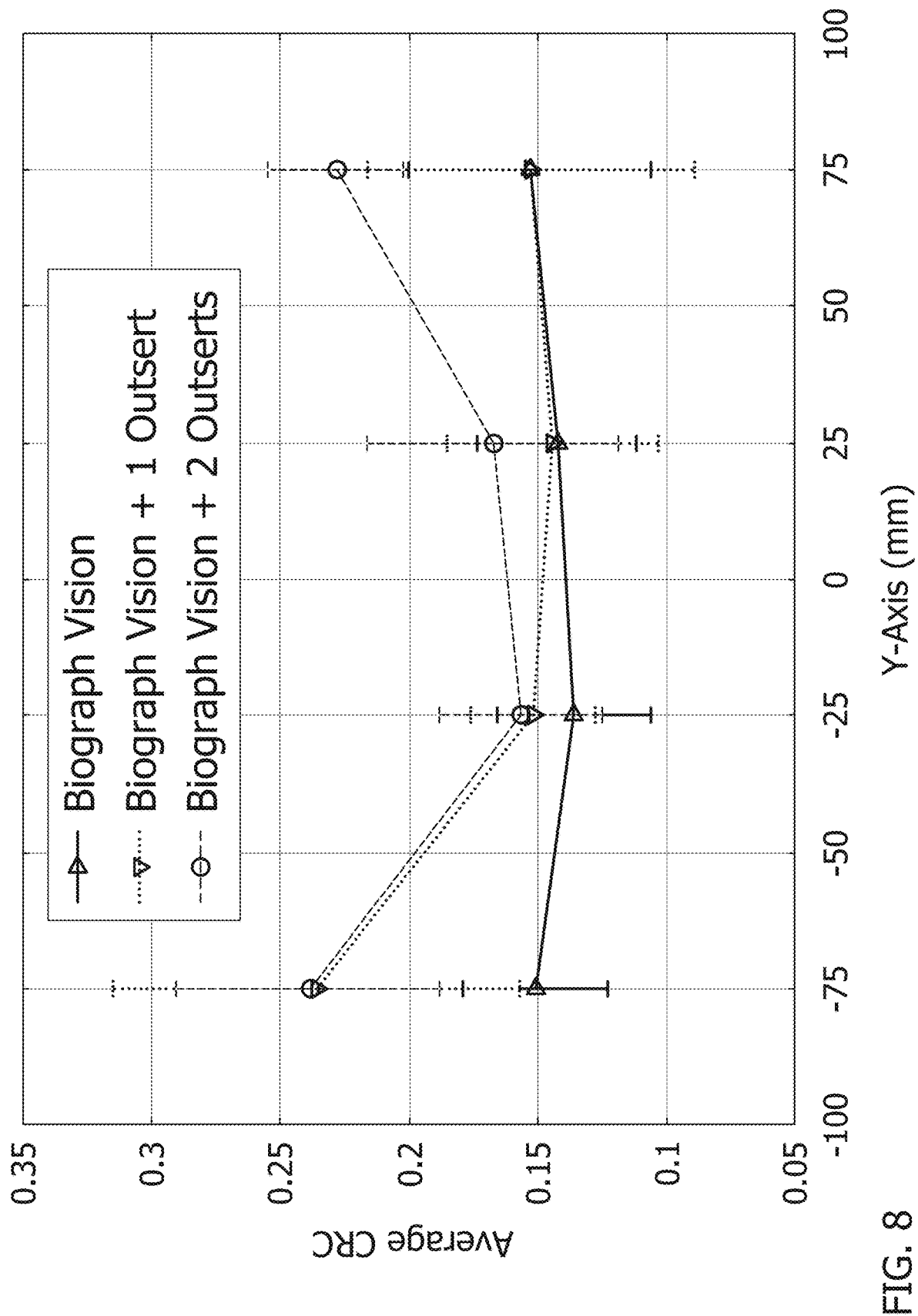
FIG. 8 is an illustration of contrast recovery coefficient (CRC) measured by a Biograph Vision™ PET scanner and the Biograph Vision™ PET scanner including one or two outserts.

FIG. 8 shows the contrast recovery coefficient of lesions in FIGS. 7C, 7D and 7E. Lesions were grouped based on their Y-coordinates, which affect the distance between the lesions and the outsert detectors. As expected, the contrast recovery coefficient was improved more significantly for lesions that are closer to the outsert detectors. For lesions that are far away from the outsert (e.g., the top row of lesions are 270 mm away from the outsert in the single-panel AWSM-PET device), the contrast recovery coefficient approaches that of the native scanner. In the case of a dual-panel AWSM-PET system, contrast recovery coefficient is enhanced more uniformly throughout the imaging FOV although still spatially variant. Since the AWSM-PET feature does not interfere with the operation of the native scanner, two sets of images are generated and can be available to physicians for review, one set of standard PET/CT images from the native scanner and one set of jointly reconstructed images using the extra AWSM-PET events. Therefore, the lesion detectability may still be improved by the technology despite the level of enhancement may not be spatially uniform.

Other design consideration: Based on the results in FIGS. 6A, 6B, and 8, a dual-panel AWSM-PET device may have more significant and more uniform improvement in system sensitivity, image resolution, and contrast recovery than a single-panel device. However, an outsert detector in close proximity above a patient's body may raise safety concerns regarding collision of a detector with the patient. The position of the upper outsert detector, therefore, should be adjusted automatically to conform to an individual patient's body geometry. This will increase enhancement in image resolution and system sensitivity.

1.3. An Image Reconstruction and Data Correction Framework for AWSM-PET System

A generalized image reconstruction framework was developed that models PET systems of arbitrary geometries. This framework includes computing a system model for PET scanners that are made of cuboidal block detectors of arbitrary geometries, automatically identifying symmetric lines of response that can share the same forward operator during image reconstruction to save computation and storage burden, and incorporating all appropriate data correction techniques for statistical image reconstruction. This reconstruction framework was used to support the development of prototype virtual-pinhole magnifying PET insert systems where the high-resolution add-on device was placed inside the scanner's imaging FOV to zoom in on an organ of interest. With the high-density detectors in the imaging FOV, several data correction techniques used for PET were re-developed and validated. In the framework, the attenuation correction is based on forward projection of a composite attenuation map using CT images of the patient and the known geometry of the virtual-pinhole magnifying detectors. Scatter contribution is estimated using a single scatter simulation technique. Random coincidences are corrected using the standard delayed-window technique offered on the PET/CT scanner. Normalization is based on a statistically-estimated model-based technique. All these algorithms have been implemented and fully validated.

To support the development of AWSM-PET technology, additional improvements to the image reconstruction framework were made. These improvements include: (1) switching from sinogram mode to fast list-mode reconstruction; (2) implementing GPU based image reconstruction and real-time system matrix computation; and (3) adding the support for TOF-PET image reconstruction. These changes may be included because some embodiments of the AWSM-PET system have nearly twice the number of crystal elements as the original scanner. Smaller image pixel size is used to reconstruct high resolution images. These changes result in a system matrix size that ranges from several hundred gigabytes to over a trillion bytes. Switching to list-mode image reconstruction and computing the system matrix in real-time by GPU reduce overall computational time by a factor of more than 10.

In one embodiment, new algorithms are developed that use the native scanner images as a prior when reconstructing the jointly estimated AWSM-PET images. This further reduces the reconstruction time. Data correction algorithms described above support the AWSM-PET geometry. The quantitative accuracy of this image reconstruction framework is validated using both Monte Carlo simulation and actual phantom experiments.

1.4. Benefits of Resolution Enhancement by the AWSM-PET technology

A Monte Carlo simulation study was conducted to evaluate how one may use the virtual-pinhole magnifying PET technology to improve cancer imaging. FIG. 9A shows a simplified torso phantom with a breast attachment being imaged by a prototype virtual-pinhole PET insert system (as shown in FIGS. 4A and 4B). FIG. 9B is a magnified view of the breast region showing 6 groups of spherical tumors (2, 3, 4, 6, 8, and 12 mm in diameter (Ø)) were placed in the breast and torso. The T/B in the phantom was varied as 3, 6, 9, or 12, respectively. The simulated acquisition time was 2.26 or 6.78 minutes. The activity concentration in the body background was 5.3 kBq/mL (143 nCi/mL), based on the assumption of 10 mCi of FDG uniformly distributed in a 70 kg patient. The PET/CT scanner simulated was a Siemens Biograph-40™ with or without the prototype virtual-pinhole magnifying PET insert attached.

FIGS. 9C and 9D show images acquired by the native scanner and by the same scanner equipped with virtual-pinhole magnifying PET technology, respectively, under various of T/B conditions. Cross comparison of these images reveals many benefits enabled by the virtual-pinhole magnifying PET technology. When T/B=3, it is difficult to detect even the biggest tumors (12 mm Ø) using the native PET scanner regardless of the scan time (2.26 or 6.78-min). In contrast, the scanner augmented with the virtual-pinhole magnifying PET can detect the 12 mm Ø tumors (marked with a red triangle) when the counting statistics are high (e.g. a 6.78-min scan) due to its improved resolution and contrast recovery. When T/B=6, the native scanner can detect 8 mm Ø tumors (marked with a green triangle) in a 6.78 min scan, but not in a 2.26 min scan. The addition of virtual-pinhole magnifying PET enables the detection of the 8 mm Ø tumors (marked with a green triangle) in a 2.26 min scan (i.e. a whole-body scan). When the T/B=9, with high counting statistics (scan time=6.78 min), the native scanner can detect 6 mm Ø tumors (marked with a blue triangle). The addition of virtual-pinhole magnifying PET enables the detection of the same sized tumors when the T/B=6 (marked with a blue triangle). When T/B=9 or 12, the addition of virtual-pinhole magnifying PET can resolve 6 or 4 mm Ø tumors in a 2.26 min scan with more confidence than the native PET scanner (marked with yellow triangles). Under all conditions, a PET scanner augmented with the virtual-pinhole magnifying PET outperforms the native PET scanner itself This study demonstrates that the virtual-pinhole magnifying PET technology can enhance the performance of a clinical PET/CT scanner for lesion detection even when the acquisition time is only 2-3 min/bed position. However, given that there are multiple ways to benefit from this technology, an imaging protocol that will achieve the best image quality for whole-body cancer imaging without disruption to the current clinical workflow will be desirable.

Continuous-bed-motion is a technology used for clinical whole-body PET/CT imaging. Instead of stop-and-go motion, patient's body is moved and scanned continuously during the whole-body PET imaging protocol. A continuous bed motion will alleviate the effect of the mismatched imaging FOV between the native scanner and the augmented outsert detectors, as illustrated in FIGS. 3A-3D. If the conventional stop-and-go motion is used, some tissues may be inside the augmented scanning zone longer than other tissues, resulting in non-uniform sensitivity profiles. Using the continuous-bed-motion technology, the body will move through the augmented scanning zone at a constant speed, resulting in a more uniform sensitivity profile. It also produces PET images with more uniform noise characteristic. Therefore the AWSM-PET imaging protocol may be implemented using the continuous-bed-motion to have those benefits.

1.5. Human Imaging Study Using AWSM-PET Technology

The AWSM-PET technology will increase the diagnostic sensitivity of FDG-PET/CT for the detection of metastatic lymph node, particularly for lesions that are smaller than the detection limit of the standard whole-body FDG-PET/CT exam. In a planned initial human imaging study, the performance of the AWSM-PET technology will be evaluated against the standard whole-body PET/CT images as to the detection of metastatic lymph nodes. The commonly accepted gold standard to evaluate the diagnostic accuracy of an imaging technology for metastatic lymph node detection is the pathology report. Therefore, the study is designed to image patients who will receive pathologic analysis of surgically dissected lymph nodes as part of their standard-of-care. For patients who have early stage diseases and are candidates for radical surgery, they typically receive a pre-surgery FDG-PET/CT scan to rule out metastases. If there is not metastatic disease based on FDG-PET/CT images, they may receive surgery and lymphadenectomy. The pathology report of the dissected lymph nodes will serve as the reference standard to assess the incremental diagnostic sensitivity of FDG-PET/CT for the detection of metastatic lymph nodes when the AWSM-PET technology is added. The population to be studied will be cancer patients who are surgical candidates and their standard of care treatment may include lymphadenectomy, and that they are scheduled to receive a whole-body PET/CT scan as standard of care to rule out metastatic diseases. The objective of the study is to measure the incremental diagnostic sensitivity of the FDG-PET/CT when the AWSM-PET technology is included for the detection of metastatic cancer.

Figure 10:
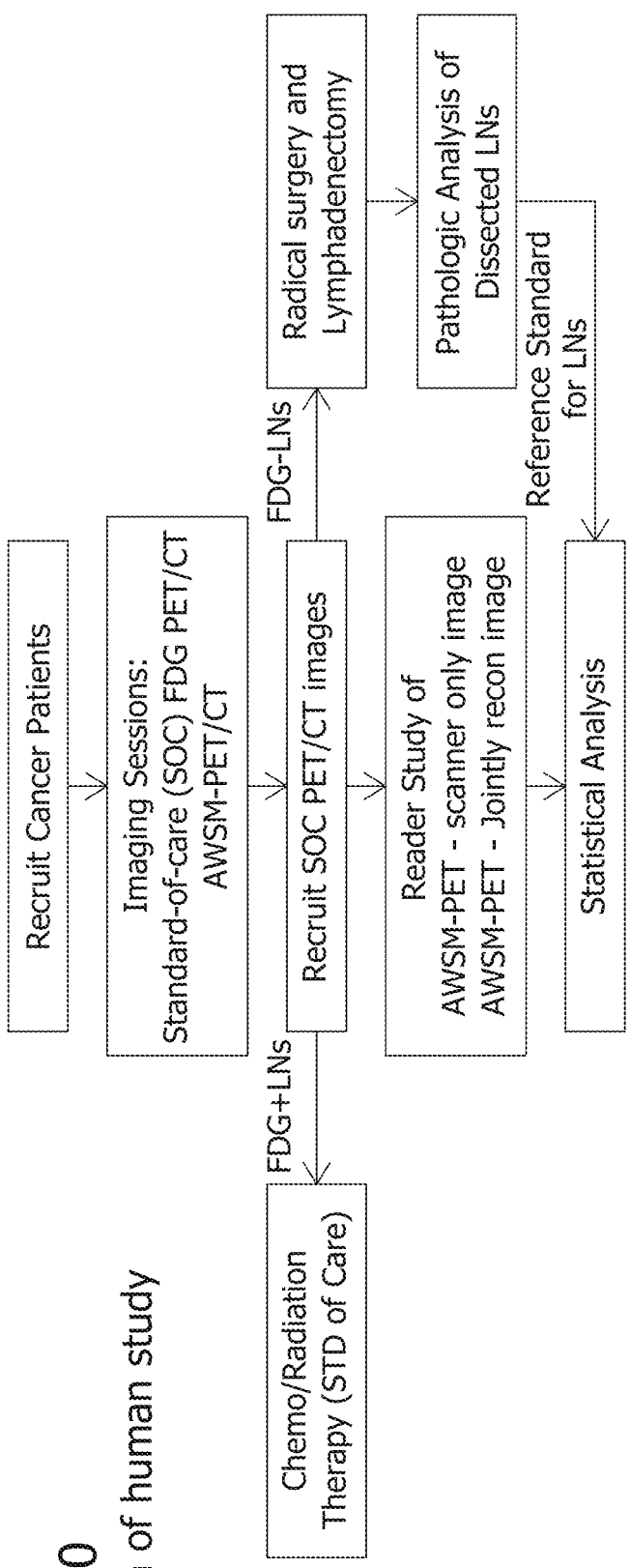
FIG. 10 is a schema of an example human study.

The overall design of a human imaging study is illustrated in the schema (FIG. 10). Cancer patients will be recruited to participate in a study that includes two imaging sessions, a standard whole-body FDG-PET/CT scan and an AWSM-PET/CT scan. Patients will continue with their standard-of-care treatment based on the result of the standard FDG PET/CT exam. Pathology reports of dissected lymph nodes from patients who receive surgery will serve as reference standard. Data acquired by the AWSM-PET protocol will be reconstructed in the following two ways. Coincidence events from the native scanner will be reconstructed using standard Siemens software to produce standard whole-body PET/CT images (designated as image 1). Coincidence events acquired by AWSM-PET outsert detectors will be added to the scanner data to jointly reconstruct AWSM-PET images (designated as image 2). Image 1 will be reviewed by two nuclear medicine physicians to make diagnosis. After a wash-out period of at least three months, images 1 and 2 will be reviewed together by the same nuclear medicine physicians to make a second diagnosis. The final evaluation will be determined by a third reader when necessary. The number of metastatic lymph nodes that are misclassified as false negative by the first read but correctly identified as true positive after the AWSM-PET images are included for the second read are counted. The results will be used to estimate the incremental diagnostic sensitivity of FDG-PET/CT for the detection of metastatic lymph nodes when the AWSM-PET technology is used. The incremental diagnostic sensitivity will be calculated on per-patient basis. Additionally, the number of sites of probable metastatic disease detected by the AWSM-PET technology will also be reported.

Example 2

Targeted Virtual-Pinhole PET (TVP-PET)

Figure 11A:
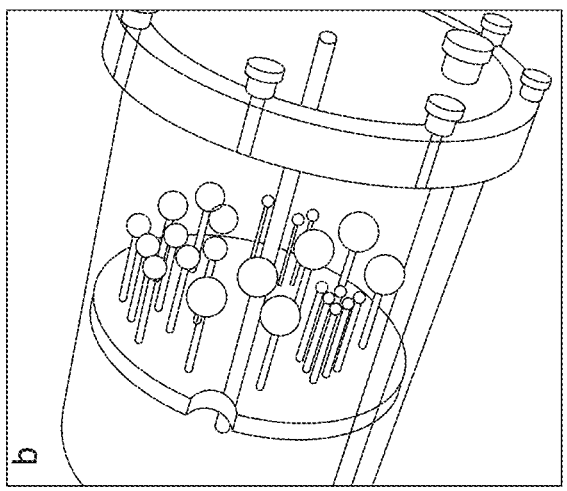
FIG. 11A is an illustration of a torso phantom that includes a breast phantom.
Figure 11B:
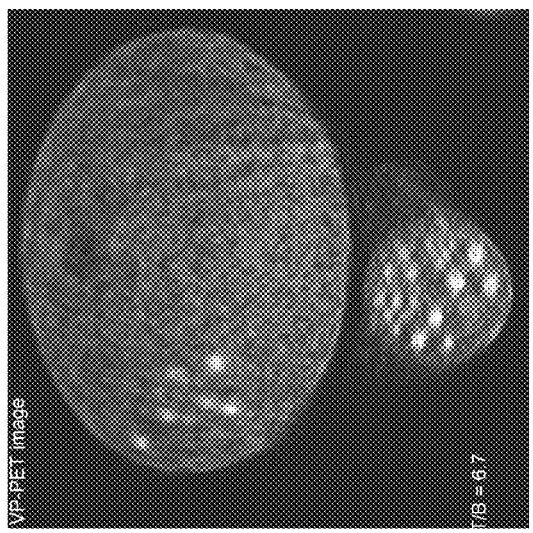
FIG. 11B is an illustration of the breast phantom of the torso phantom shown in FIG. 11A.
Figure 11C:
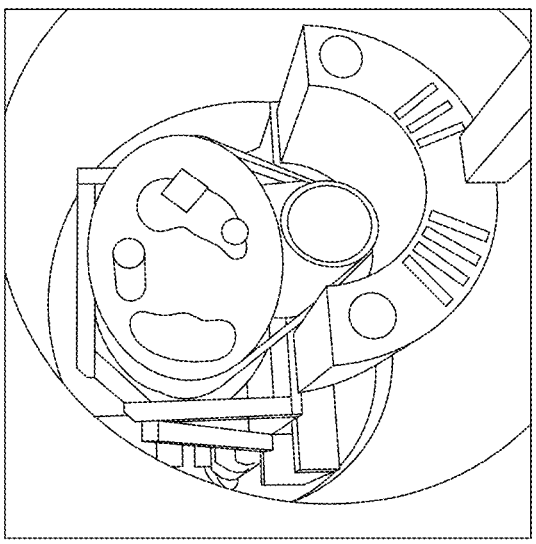
FIG. 11C is an image of the torso phantom shown in FIG. 11A that is acquired by scanner detectors.
Figure 11D:
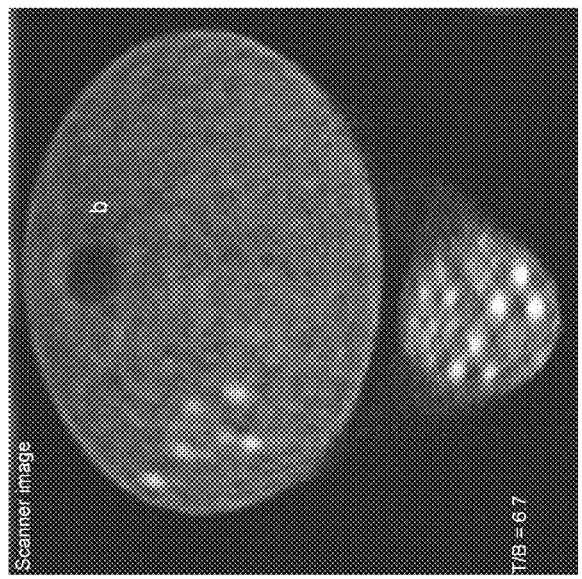
FIG. 11D is an image of the torso phantom shown in FIG. 11D that is acquired by a VP-PET scanner.

The example virtual-pinhole PET (VP-PET) systems bring the benefits of organ-specific PET to a clinical PET/CT scanner. In such systems, by establishing coincidence detection between a set of high-resolution PET detectors and a PET scanner, each high-resolution detector can act as an electronic pinhole collimator to improve the image resolution of a whole-body PET scanner. Several prototype VP-PET insert devices were developed, which demonstrated the feasibility of improving the image resolution of a clinical PET/CT scanner without compromising its body imaging capability. FIG. 11A shows a torso phantom with a breast phantom attachment positioned in the field of view of a Siemens Biograph 40 PET/CT scanner. A prototype virtual-pinhole magnifying PET insert system, as illustrated in FIGS. 4A-4D, was positioned near the breast phantom attachment to enhance the image resolution of the organ-of-interest, which is a breast in this case. FIG. 11B shows a breast phantom by itself. The breast phantom includes spherical tumors. The breast compartment includes spherical tumors of various sizes ranging from 3.59 mm to 11.4 mm in diameter and filled with radioactivity having T/B=6. Additionally, there are spherical tumors in the torso phantom with sizes ranging from 3.59 mm to 11.4 mm in diameter. The body imaging capability was preserved while improving the image resolution and tumor contrast using the virtual-pinhole magnifying PET insert technology. FIG. 11C shows an image acquired by the scanner. FIG. 11D shows an image at the same location as FIG. 11C acquired by virtual-pinhole magnifying PET. Results in FIGS. 11C and 11D demonstrate that the virtual-pinhole magnifying PET technology improves image resolution within the breast section of the phantom. The level of improvement is consistent with those observed in the Monte Carlo simulation study in FIGS. 9C and 9D. The virtual-pinhole magnifying PET technology enhances tumor contrast in not only the breast compartment but also the torso despite the level of improvement diminishes for tissues farther away from the insert detectors. This advantage over organ-specific PET imagers allows the technology to be extended for whole-body cancer imaging using targeted virtual-pinhole PET (TVP-PET).

Figure 12A:
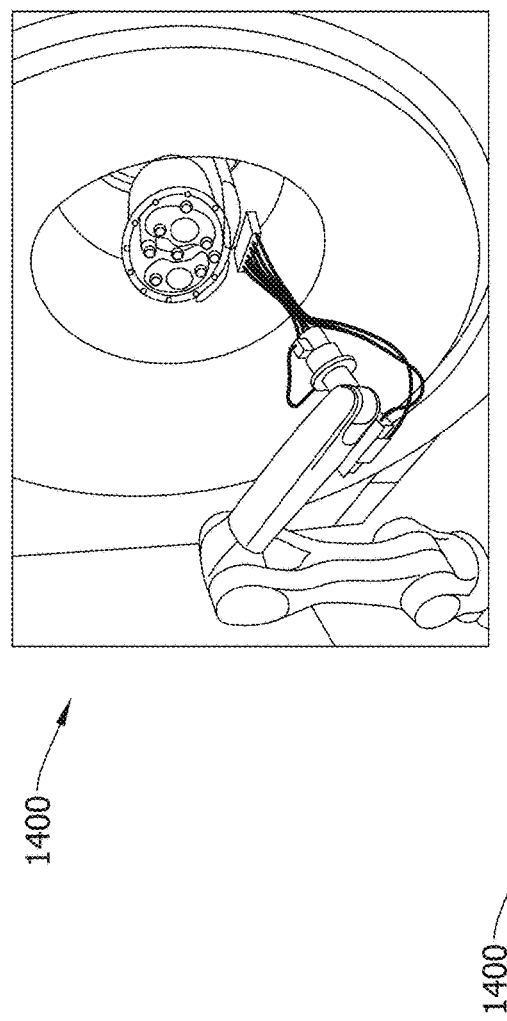
FIG. 12A is a partial rear perspective view of another example PET scanner system that uses targeted VP-PET (TVP-PET) technology.
Figure 12B:
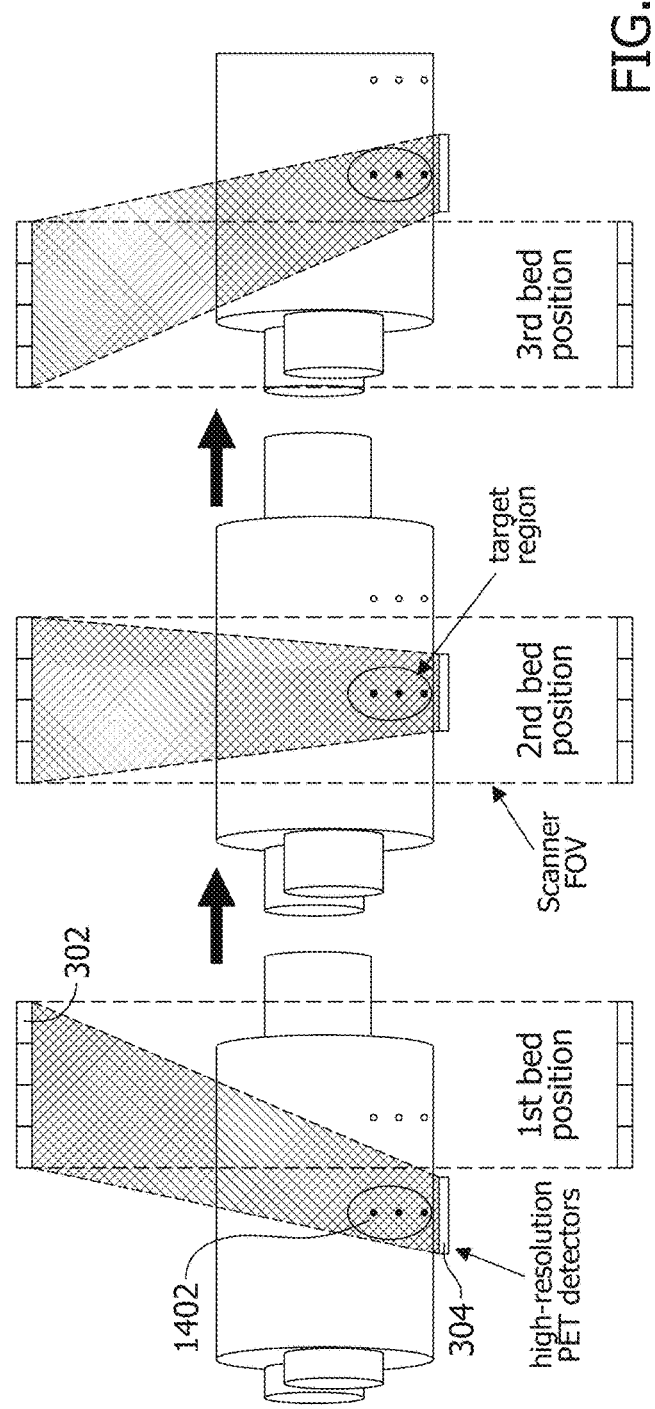
FIG. 12B is an illustration of the FOVs covered by scanner detectors and high-resolution detectors of the system shown in FIG. 12A as a target region moves through the FOV of the scanner detectors.

A second-generation VP-PET insert system or targeted VP-PET system 1400 (FIGS. 12A-12B) was constructed with several technical advances that may make it more suitable for, among other things, human imaging studies. System 1400 includes detector array 302 and detector panel 304. Different from PET system 300, in system 1400, detector panel 304 is positioned proximate to a target region 1402 of a subject and follows target region 1402 during the scanning by PET system 1400. As a result, detector panel 304 is outside the FOV covered by detector array 302 during at least a portion of scanning by system 1400. FIG. 12A is a second-generation VP-PET prototype with an integrated robotic arm that can position a flat-panel detector at an arbitrary location around a patient's body. FIG. 12B is a schematic drawing showing the principle of the Targeted VP-PET (TVP-PEP) imaging. A patient is moved across the scanner's imaging FOV (illustrated by the dash lines) in multiple bed positions for whole-body imaging. The high-resolution detectors in a VP-PET device are moved by a robotic arm controlled by control unit 106 to follow the target region as the patient is moved across the scanner. In some embodiments, the high-resolution detectors may be moved manually. In some other embodiments, the high-resolution detectors may be embedded in the patient bed and moved across the scanner FOV along with the patient's body during whole-body PET/CT imaging. The shaded blue areas show the imaging FOV of the VP-PET device. With the combination of high-resolution detectors with detectors of the whole-body scanner, the target region is scanned by the VP-PET detectors from multiple angles, effectively boosting the counting statistics from the target region by several folds.

Taking advantage of the fully integrated robotic arm in this second-generation VP-PET device, a specific region of a body is targeted and followed during a whole-body PET/CT scan. This strategy not only enhances the image resolution but also increases the counting statistics of the data from a high-risk target region, such as the pelvis for cervical cancer patients, or the axilla and/or contralateral breast for breast cancer patients. FIG. 12B is an illustration of the principle of the TVP-PET. The high-resolution PET detectors may be placed close to a patient's body to "zoom in" on a user-selected target region. The TVP-PET detectors follow the target region as the patient is moved across the scanner's imaging FOV during a whole-body imaging protocol. As the target region approaches and leaves the native scanner's imaging FOV, the VP-PET detectors are placed just outside the scanner's detector rings in the axial direction (e.g., at bed positions #1 and #3 in FIG. 12B). When the target region is in the scanner's imaging FOV, the VP-PET detectors are placed inside the scanner as a typical VP-PET insert device (e.g., at bed position #2). Using this targeted imaging approach, the VP-PET detectors will collect extra coincidence events originated from the target region when the patient's body is at bed positions #1 and #3. All coincidence events detected by the VP-PET detectors will be incorporated with the native scanner's data for joint image reconstruction. The results will be a set of whole-body PET images with significantly improved image resolution, counting statistics, and noise characteristics in the target region. These benefits can be gained without incurring any additional scan time or slowing down the clinical workflow when the TVP-PET technology is adopted by PET/CT manufacturers.

The TVP-PET technology complements PET, PET/CT, or PET/MRI scanners. It works hand-in-hand with any PET/CT scanner (including TOF-PET and digital PET that employ advanced reconstruction algorithms) to further improve their native image resolution and sensitivity. It should be noted that the TVP-PET technology may be implemented by a manufacturer without a complicated robotic arm design. A robotic arm is used to position high-resolution detectors because it offers the maximum flexibility and allows us to use the prototype VP-PET device to explore different applications. The high-resolution detectors may be embedded in the patient bed and made moveable along the axial direction relative to a patient's body in order to implement the proposed target-tracking feature. This will avoid the complexity and cost of a robotic arm while maintaining the TVP-PET functionality.

The effect of improved detector spatial resolution versus timing resolution on lesion detectability under a whole-body imaging condition was analyzed. The results demonstrate that even under limited counting statistics when using the whole-body imaging protocol (i.e., 2-3 minutes per bed position) one can still improve lesion detectability by enhancing image resolution using detectors of higher spatial resolution or by enhancing the signal-to-noise ratio (S/N) using detectors of better timing resolution. An increased lesion detectability is achieved when one improves both spatial resolution of a scanner and the S/N ratio of the data. Therefore, technologies such as the TVP-PET that can overcome the fundamental resolution limit of whole-body PET (approximately 2 mm FWHM) and also enhance the S/N of PET images may be valuable for clinical PET applications.

The TVP-PET imaging technology was validated using a prototype VP-PET insert device and a research PET/CT scanner (Biograph 40™). The device has an integrated robotic arm (FIG. 12A) that can position the high-resolution detector panel at arbitrary locations around a patient's body.

Figure 13B:
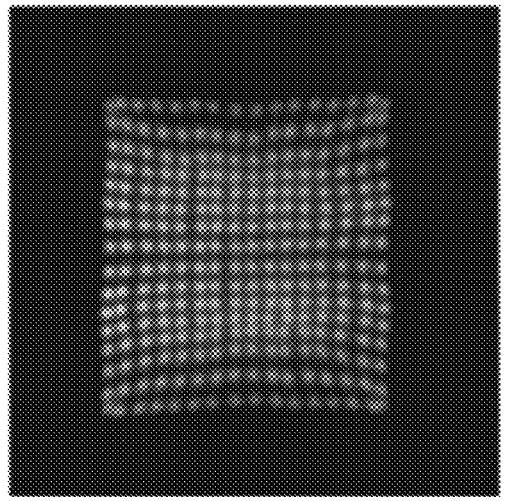
FIG. 13B is a flood image of the detector module shown in FIG. 13B that is read out by PET/CT scanner electronics.
Figure 13A:
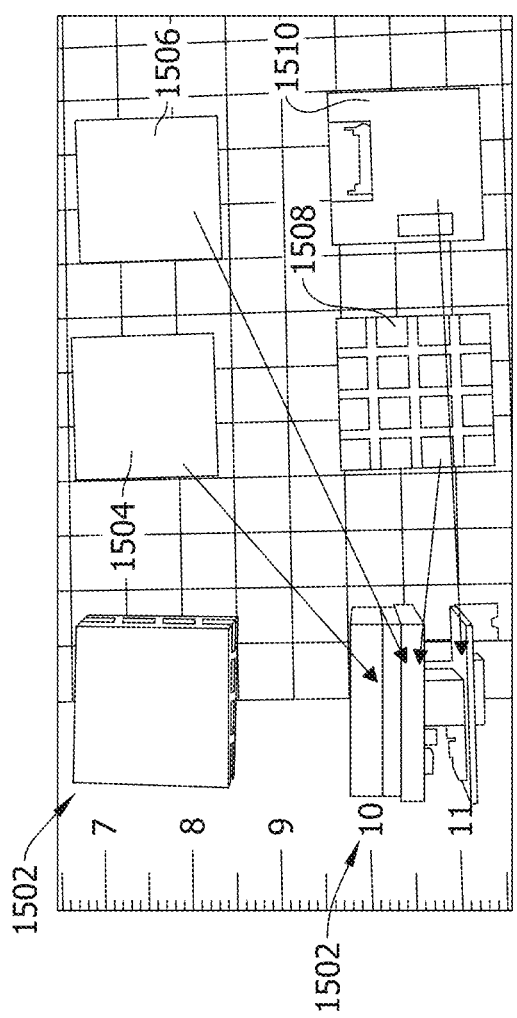
FIG. 13A is an illustration of an example a compact PET detector module.
Figure 13C:
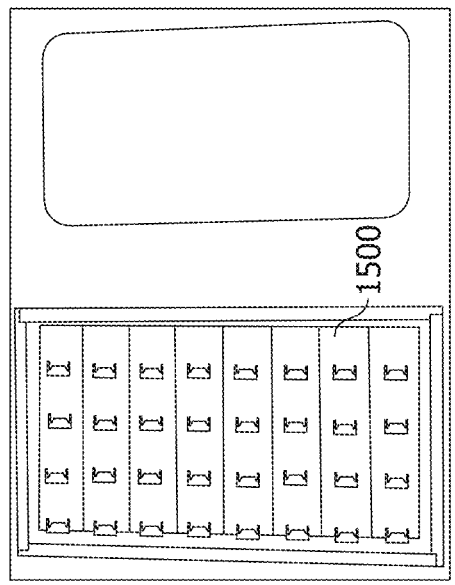
FIG. 13C is a front view of the detector module shown in FIG. 13A with its cover removed and a cell phone placed next to for size reference.

A flat-panel VP-PET device with compact PET detectors of sub-millimeter intrinsic resolution. FIGS. 13A-13C show an example high-resolution PET detector. FIG. 13A is an illustration of a SiPM-based high-resolution compact PET detector module 1502. Top (top left of FIG. 13A) and perspective (Bottom left of FIG. 13A) views of detector module 1502 are provided in FIG. 13A. FIG. 13B shows a representative flood image of a detector module read out by PET/CT scanner electronics. FIG. 13C shows the flat panel detector 1500 with its carbon fiber cover removed. A cell phone having a 5.5" (14.0 cm) screen is placed next to the detector 1500 as a size reference. The new VP-PET device employs a flat-panel geometry to allow more flexibility in positioning the detectors around a patient's body.

In the example embodiment, the flat-panel detector 1500 includes 32 PET detector modules 1502 arranged in a 4×8 array (FIG. 13C). Detector module 1502 includes a 16×16 lutetium yttrium orthosilicate (LYSO) array 1504, an acrylic light guide 1506, a custom silicon photomultiplier (SiPM) array 1508, and a printed circuit board 1510 for signal multiplexing with a charge-division resistor network and connectors. The LYSO array 1504 includes 16×16 elements of 0.92×0.92×3 mm crystal, arranged in 1 mm pitches to provide sub-millimeter intrinsic spatial resolution. FIG. 13B shows the flood image of the detector when it is exposed to a uniform flux of 511 keV γ-rays. All crystal elements are clearly resolved. For example, the energy resolution of the detector module is 10.2±0.7% FWHM for 511 keV γ-rays. The timing resolution of the detector is 0.95±0.08 ns FWHM when measured against a reference fast detector. These characteristics match well with that of a Siemens Biograph 40™ PET/CT scanner. Moreover, these SiPM-based PET detectors are compact (less than 15 mm total thickness) and can be packaged to form large sensing areas with minimal gaps between modules (<mm in this device). The enclosure of the flat panel is made of carbon fiber plates to minimize the weight and attenuation to γ-ray signal. The overall dimension of the flat-panel enclosure is 150×81×23 mm (L×W×H). The sensitive area of the flat-panel device 1500 is 135×67 mm (L×W). The image resolution of the PET scanner equipped with the new VP-PET device is estimated to be equal to or better than 2 mm FWHM within 17.5 cm from the front surface of the flat panel detector using Eq. 1 shown in Example 1 above. In Eq. 1, $d_1$ is the distance from target to the panel detector; $d_2$ is the distance from the target to the scanner detectors; $w_1$=1 mm and $w_2$=4 mm are the crystal width of the VP-PET and scanner crystals, respectively. At a distance farther than 17.5 cm, the resolution is worse than 2 mm FWHM, but still better than the native resolution of the PET scanner.

Expanded system electronics to support the augmented functionality. New add-on electronics and firmware were developed to support the VP-PET technology using a previous generation PET/CT scanner (Siemens Biograph 40). A set of switch boards were added to the scanner to support additional electronics to decode signals from VP-PET detectors, where the system may include up to 96 PET detector modules. New firmware can be loaded to the scanner on-demand to enable coincidence detection between the VP-PET device and the scanner. These expansions allow full preservation of the sensitivity and functionality of the native PET/CT scanner, with an option to turn ON or OFF the additional VP-PET capability using a simple batch command. With additional detectors in the VP-PET device, the augmented PET/CT scanner will detect more annihilation γ-rays than the original PET/CT scanner. The VP-PET technology can be easily translated to scanners that have reserved additional electronics channels, such as Siemens Biograph Vision™ PET/CT or scanners that have expandable system architecture.

Figure 14B:
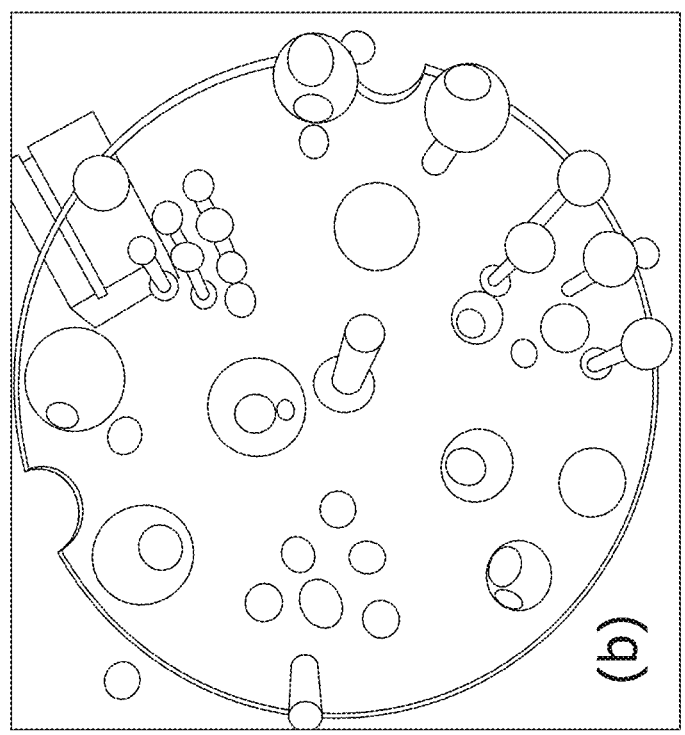
FIG. 14B is an illustration of the torso phantom shown in FIG. 14 having fillable lesions of various sizes.
Figure 14A:
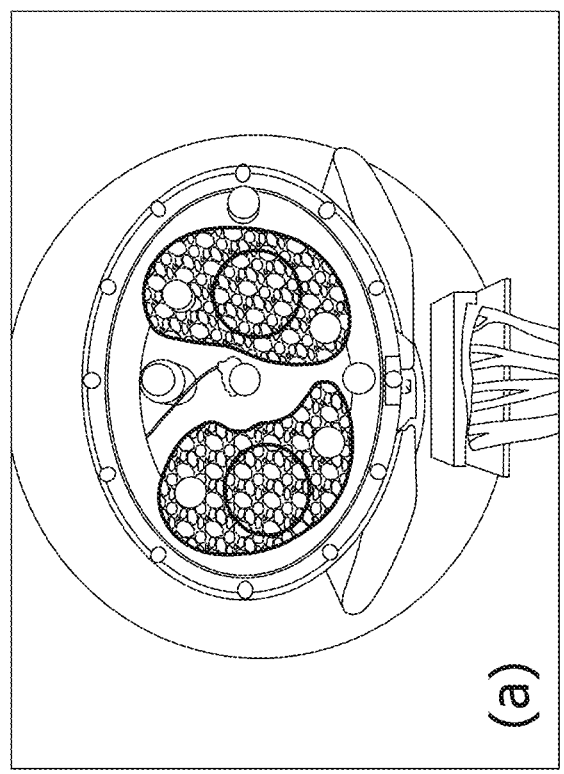
FIG. 14A is an illustration of a setup of a torso phantom imaging experiment with a VP-PET insert placed underneath the patient table.

Body phantom study by the second-generation VP-PET device. A body phantom with small lesions of various sizes was imaged to evaluate the enhancement of the contrast recovery coefficient (CRC) by the second-generation VP-PET device. The phantom is a Data Spectrum Elliptical Lung-Spine Torso Phantom that measures 316×228×162 mm³, as shown in FIG. 14A. A panel of fillable spherical glass tumors (FIG. 14B) was mounted inside the torso phantom. The diameters of the 6 clusters of tumors are 3.3, 4.3, 6.0, 8.0, 9.6, and 11.4 mm, respectively. Only three spheres in each size group were filled with radioactivity and blue dyes, and other spheres in the size group contain water only.

Figure 15A:
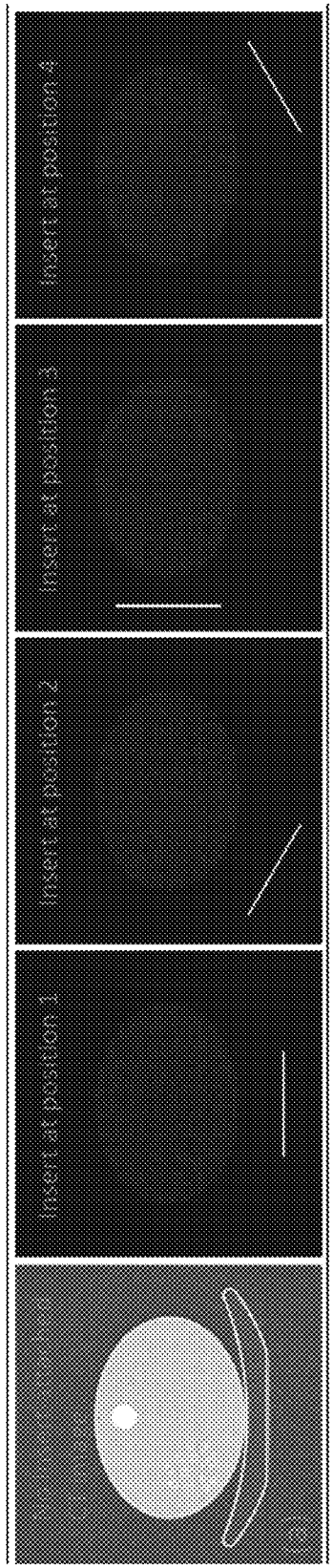
FIG. 15A is an illustration of scanner setups of a torso phantom imaging study.
Figure 15B:
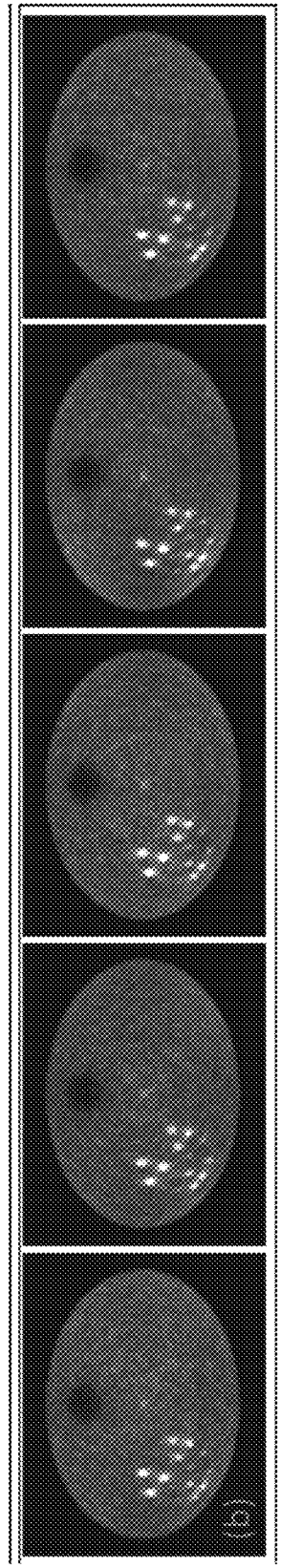
FIG. 15B are images corresponding to the scanner setups shown in FIG. 15A.

The torso phantom and the spherical tumors were filled with $^{18}$F solutions that include an initial activity concentration of 3.63 kBq/mL and 21.78 kBq/mL, respectively, to obtain a tumor-to-background ratio of 6. The flat-panel detector were placed at 4 different locations (as illustrated in FIG. 15A) and scanned the torso phantom 300 s at each location (adjusted for the decay of $^{18}$F). The VP-PET detectors were either unattached or positioned around the torso phantom at 4 different locations (FIG. 15A). FIG. 15B shows corresponding reconstructed images using an acquisition time equivalent to 200 s during a typical clinical FDG scan. This is equivalent to a 200 s body scan at each panel location when 370 MBq FDG is uniformly distributed in a 70 kg patient. Subsequently, the VP-PET insert device was removed and the phantom was imaged again by the native PET scanner for a duration of 200 s-equivalent after decay correction. A CT scan of the phantom was also acquired for attenuation correction.

Figure 16A:
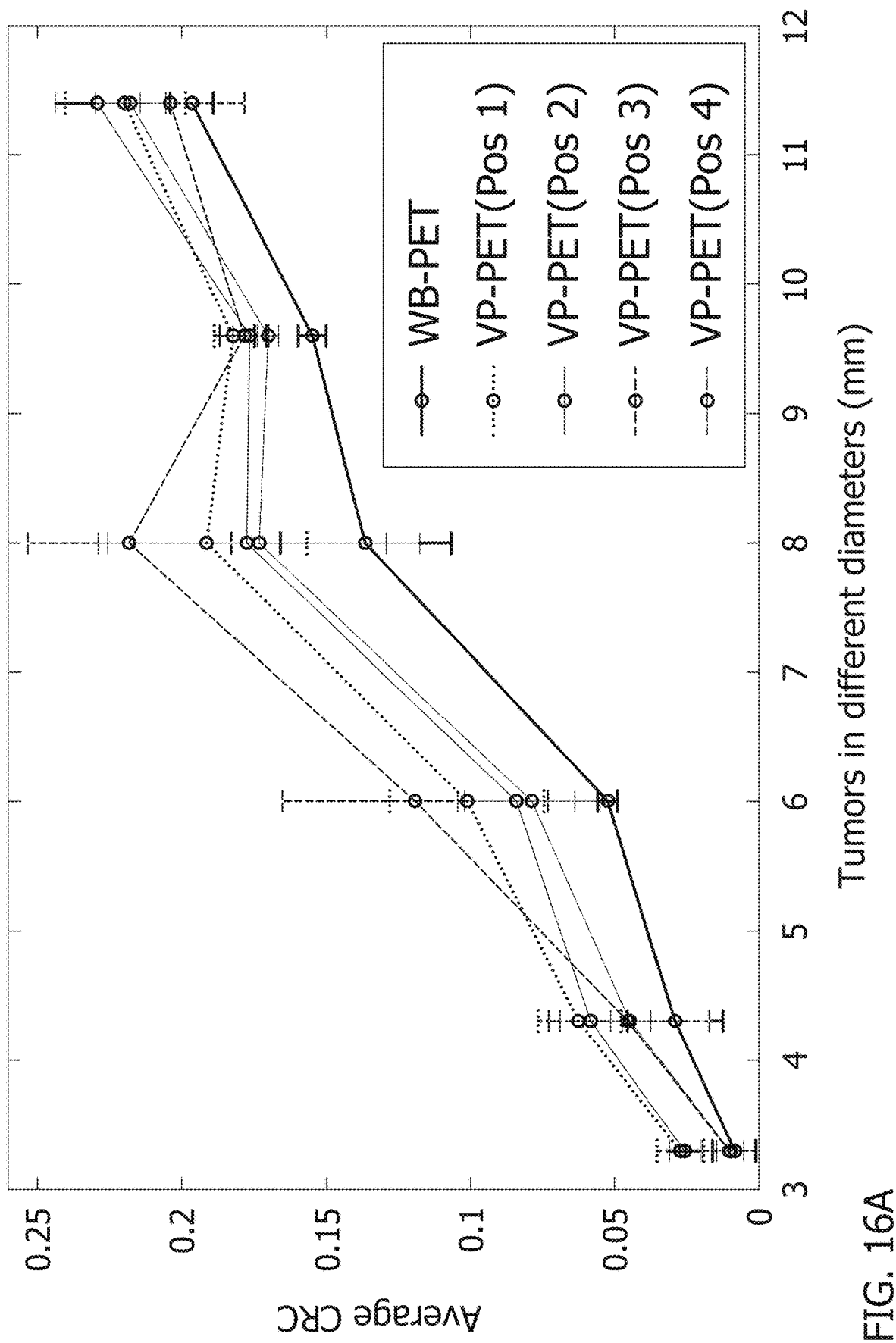
FIG. 16A is an illustration of the mean and standard deviation of CRC as a function of tumor sizes of the phantom used for FIGS. 15A and 15B.
Figure 16B:
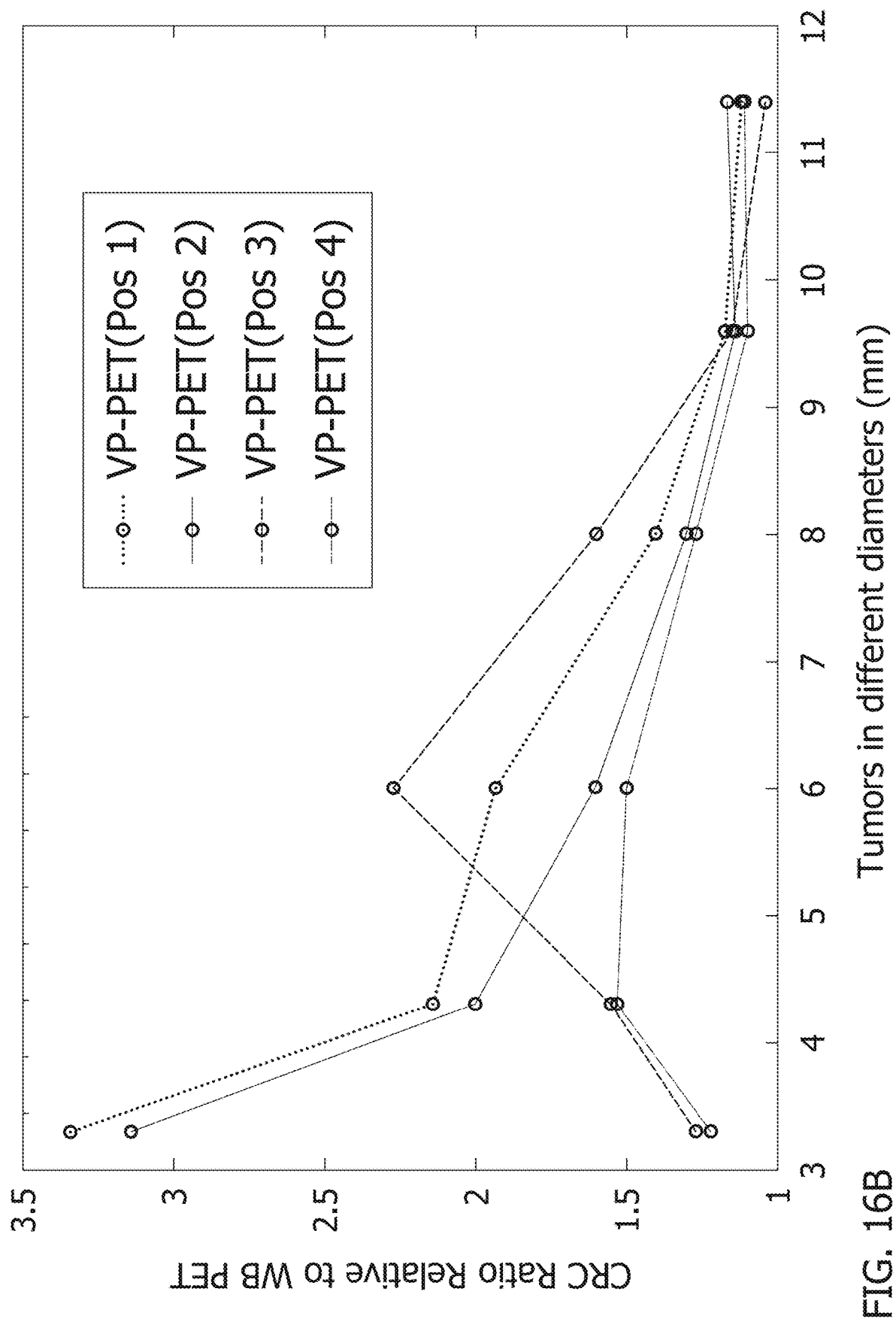
FIG. 16B is an illustration of the ratio of CRC with and without the VP-PET technology.

All images were reconstructed using the above graphic processing unit (GPU)-based reconstruction platform. FIG. 15B shows the reconstructed images from the 5 configurations after 30 iterations. Visible improvement is observed in tumor contrast when the high-resolution VP-PET insert was employed, especially for the smaller tumors. A spherical volume-of-interest (VOI) of the same diameter as each tumor was used to estimate the mean count density $C_{T,i}$ for each tumor. The center location of each tumor was determined from the co-registered CT images. The background count density $C_{B,i}$ was determined as the mean number of counts in a large square VOI over 20 adjacent slices. The $CRC_i$ for the i-th tumor was calculated according to the NEMA NU2-2001 definition as shown below:

$$CRC_i = 100\% \times \frac{\left(\frac{c_{T,i}}{c_{B,i}} - 1\right)}{(\text{uptake} - 1)}, \quad (2)$$

where uptake is 6 in this study. FIG. 16A shows the mean and standard deviation of CRC as a function of tumor sizes of the phantom shown in FIGS. 14A-14B. FIG. 16B shows the ratio of CRC with and without the VP-PET technology. The CRC is averaged over of the tumors of the same diameter and presented as a function of tumor sizes in FIG. 16A.

From the native scanner images, the average CRCs are 0.82%, 2.90%, 5.25%, and 13.63% for tumors with diameters of 3.3, 4.3, 6.0, and 8.0 mm, respectively. The 3.3 mm and 4.3 mm diameter tumors have the best average CRC of 2.73% and 6.21%, respectively, when the VP-PET detectors are at position 1. The 6.0 mm and 8.0 mm diameter tumors have the best average CRC of 11.92% and 21.81%, respectively, when the VP-PET detectors are at position 3. For tumors with larger diameters (e.g. 9.6 mm and 11.4 mm), the enhancement in average CRC is less significant regardless where the VP-PET detectors are placed. This is because the image resolution of the native scanner is adequate in recovering the contrast of the larger tumors.

The results demonstrate the improvement in tumor contrast improvement by the VP-PET technology, particularly for smaller lesions. Comparison of results from different panel-locations show that the resolution and CRC enhancement depend on both the source location and the VP-PET panel location. When the panel is placed far away from the target region (e.g., position 4 in FIG. 15A), the level of enhancement is reduced. Placing the panel detectors below a patient's body (position #1 in FIG. 15A) is a logical choice considering that cancers may metastasize to either side of a patient's body. Based on FIG. 16B, the panel location 1 also offers significant enhancement to the CRC for lesions at most locations. As a result, the VP-PET detectors is placed below a patient's body (position #1 in FIG. 15A) to evaluate the TVP-PET technology.

1. Functionality and Reproducibility of the TVP-PET Technology

To implement the proposed TVP-PET technology, the same torso phantom with spherical lesions is scanned using the second-generation VP-PET device based on the targeted imaging protocol as illustrated in FIG. 12B. The torso phantom will be moved across the scanner's native imaging FOV and imaged at multiple bed positions (minimum of 3 beds). The robotic arm is used to place the flat-panel detector under the patient bed and move the detector along the axial direction to follow the section of the phantom that includes the clusters of spherical lesions ("target"). The scan time per bed position is kept the same as that of the standard-of-care whole-body imaging protocol. With the custom firmware and software, the high-resolution coincidence events are simultaneously acquired using the VP-PET detectors as the scanner acquires regular whole-body PET imaging data. This tracking and imaging strategy is expected to improve the counting statistics from the target region by approximately a factor of three if the protocol in FIG. 12B is used when compared to the original VP-PET technology. Coincidence events from the native scanner and the high-resolution events from all three bed positions are combined for joint image reconstruction. This should further improve the image resolution and CRC of tumors when compared to the images shown in FIG. 15B.

Figures 17A, 17B, 17C:
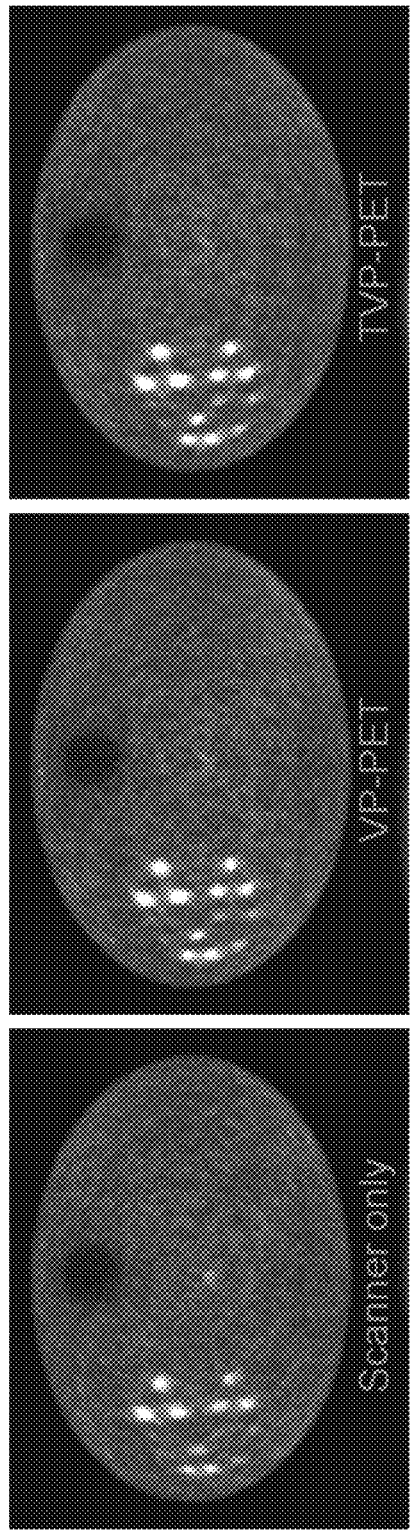
FIG. 17A is an image of the phantom shown in FIG. 14A that is acquired by scanner detectors of a PET/CT scanner.
FIG. 17B is an image of the phantom shown in FIG. 14A that is acquired by the PET/CT scanner equipped with a VP-PET technology having flat-panel detectors placed below a patient table.
FIG. 17C is an image of the phantom shown in FIG. 14A that is acquired by the PET/CT scanner equipped with the VP-PET technology used for FIG. 17B and using a TVP-PET protocol.

In a preliminary test, the torso phantom was filled with $^{18}$F solution using a tumor-to-background ratio of 6 for the spherical lesions. The phantom was first imaged using the native PET/CT scanner. Then the phantom was imaged with the VP-PET detectors centered in the scanner's imaging FOV (i.e., the original VP-PET technology). Finally, the phantom was imaged using the TVP-PET protocol in FIG. 12B. Results are shown in FIGS. 17A-17C. FIGS. 17A-17C are images of the torso phantom with spherical tumors imaged by a PET/CT scanner, the same scanner equipped with VP-PET, and the native scanner with the flat-panel detectors placed under the patient bed (i.e., the position as shown in FIG. 12A) using a TVP-PET protocol as shown in FIG. 12B, respectively.

Figure 18A:
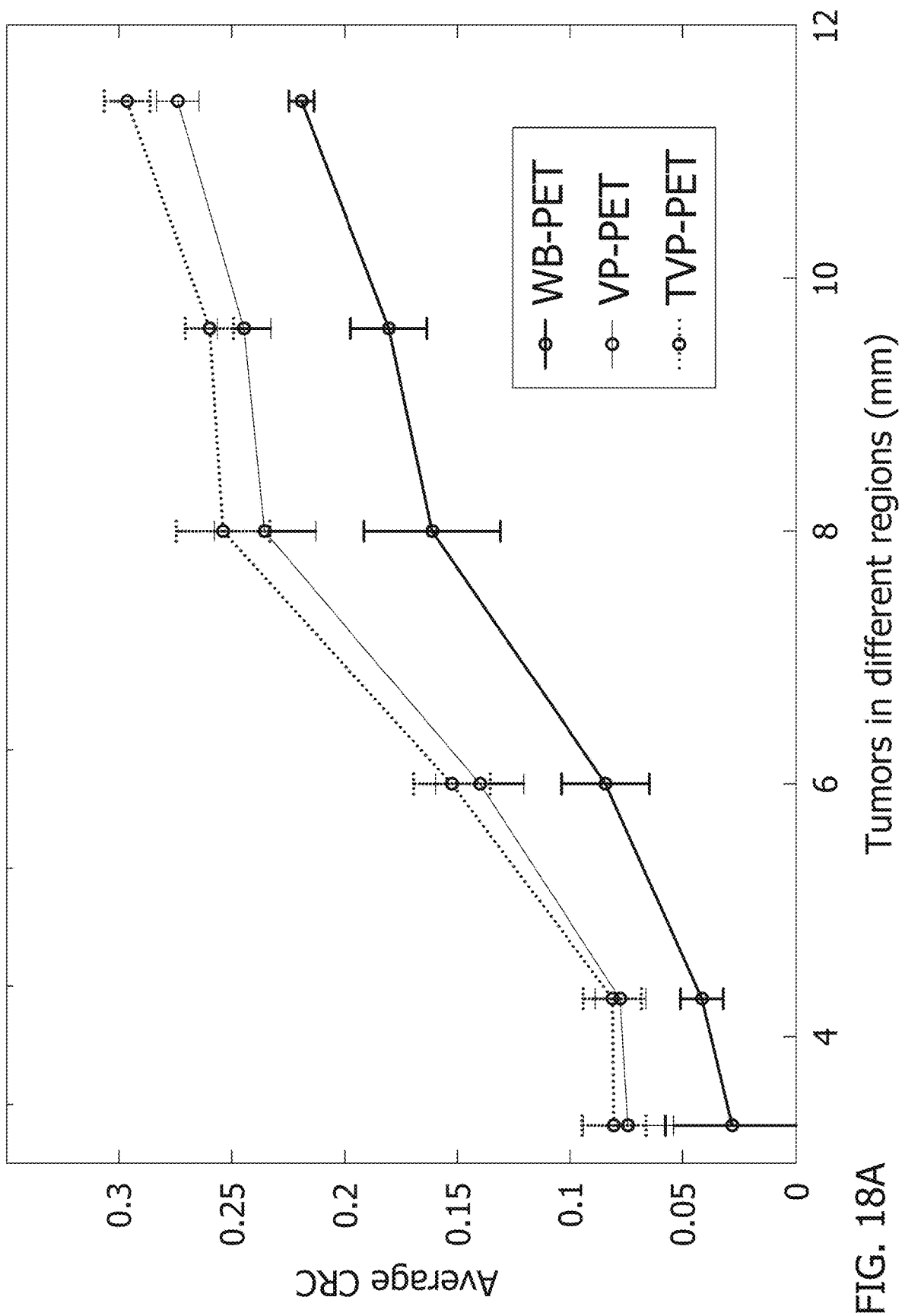
FIG. 18A is an illustration of the mean and standard deviation of CRC as function of tumor sizes of the phantom shown in FIG. 14A.
Figure 18B:
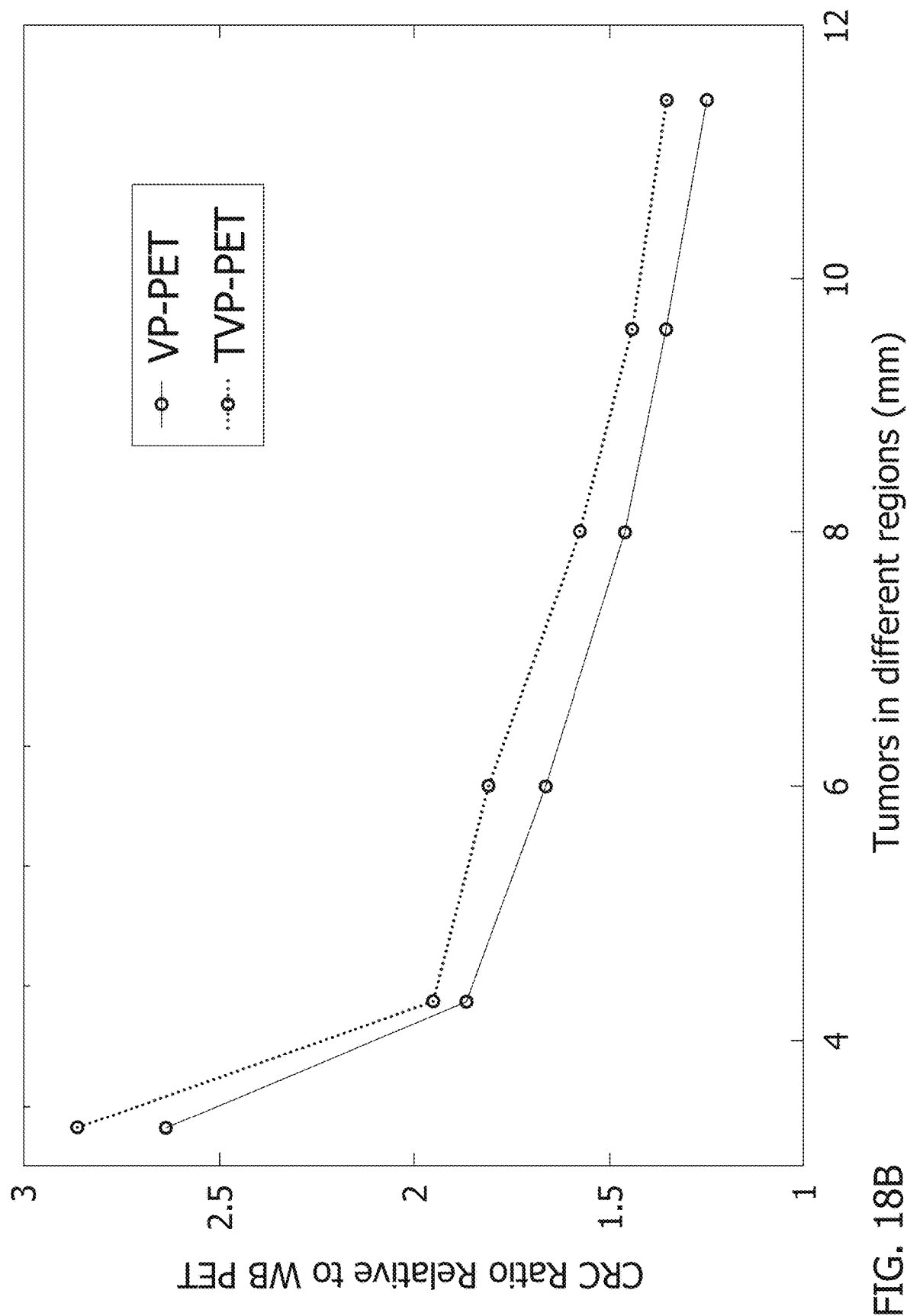
FIG. 18B is an illustration of the ratio of CRC for VP-PET and TVP-PET relative to the native whole-body PET/CT scanner.

The average CRC were computed for each group of tumors of the same size. FIG. 18A shows the average CRC as a function of tumor size for each of the 3 scanner configurations. FIG. 18B shows the ratio of the CRC from the VP-PET images (or TVP-PET images) over CRC from the standard PET/CT images for each size of tumors. As shown, smaller lesions suffer more from partial volume effect and have poorer CRC. The VP-PET technology improves the CRC when compared to the native scanner. The TVP-PET technology further improves the CRC when compared to the VP-PET technology.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

Although described in connection with an example computing system environment, embodiments of the invention are operational with numerous other general purpose or special purpose computing system environments or configurations. The computing system environment is not intended to suggest any limitation as to the scope of use or functionality of any aspect of the invention.

Embodiments of the invention may be described in the general context of computer-executable instructions, such as program modules, executed by one or more computers or other devices. The computer-executable instructions may be organized into one or more computer-executable components or modules. Generally, program modules include, but are not limited to, routines, programs, objects, components, and data structures that perform particular tasks or implement particular abstract data types. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein. Aspects of the invention may also be practiced in distributed computing environments where tasks are performed by remote processing devices that are linked through a communications network. In a distributed computing environment, program modules may be located in both local and remote computer storage media including memory storage devices.

While example embodiments of components, assemblies and systems are described, variations of the components, assemblies and systems are possible to achieve similar advantages and effects. Specifically, the shape and the geometry of the components and assemblies, and the relative locations of the components in the assembly, may be varied from that described and depicted without departing from inventive concepts described. In addition, in certain embodiments certain components in the assemblies described may be omitted to accommodate particular applications and installations, while still providing improved systems.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A positron emission tomography (PET) system for imaging a target region of a subject, the system comprising:
   a detector array comprising an array of gamma ray detectors defining a field of view and configured to detect at least one coincidence event;
   a detector panel comprising an array of gamma ray detectors having higher resolutions than the detector array and positioned in closer proximity to a patient table than the detector array, the detector panel positioned outside the field of view defined by the detector array during at least a portion of scanning by the PET system, the detector panel configured to detect at least one coincidence event in cooperation with the detector array; and
   a control unit configured to be in communication with the detector panel and the detector array and configured to control the detector array and the detector panel to operate in cooperation with each other.

2. The system of claim 1, wherein the detector panel further comprises an outsert positioned outside the field of view defined by the detector array during entire scanning by the PET system.

3. The system of claim 2, further comprising at least one additional detector panel positioned in closer proximity to the patient table than the detector array, wherein the at least one additional detector panel is in communication with the control unit and is configured to detect at least one additional coincidence event in cooperation with the detector array and the detector panel.

4. The system of claim 1, wherein the detector panel is movable across the field of view defined by the detector array during scanning by the PET system.

5. The system of claim 4, wherein the detector panel is positioned in closer proximity to a target region in the subject than the detector array, and the detector array remains stationary relative to the target region during the scanning by the PET system.

6. The system of claim 1 further comprising a patient table on which the subject lies during scanning by the PET system, wherein the detector panel is positioned below the patient table during the scanning by the PET system.

7. The system of claim 1, wherein the control unit is configured to generate an image of the target region based on the at least one coincidence event detected by the detector array and the at least one coincidence event detected by the detector panel.

8. A device to enhance an image resolution of a positron emission tomography (PET) system, the PET system configured to image a target region of a subject, the device comprising:
   a detector panel comprising an array of gamma ray detectors having higher resolutions than detectors of a detector array of the PET system and positioned in closer proximity to a patient table than the detector array, the detector panel to be positioned outside a field of view defined by the detector array during at least a portion of scanning by the PET system and configured to detect at least one coincidence event in cooperation with the detector array, wherein the detector panel is configured to be in communication with a control unit of the PET system, the control unit configured to be in communication also with the detector array and configured to control the detector array and the detector panel to operate in cooperation with each other.

9. The device of claim 8, wherein the detector panel further comprises an outsert to be positioned outside a field of view defined by the detector array during entire scanning by the PET system.

10. The device of claim 9, further comprising at least one additional detector panel to be positioned in closer proximity to the patient table than the detector array, wherein the at least one additional detector panel is configured to be in communication with the control unit and is configured to detect at least one additional coincidence event in cooperation with the detector array and the detector panel.

11. The device of claim 8, wherein the detector panel is configured to be movable across the field of view defined by the detector array during scanning by the PET system.

12. The device of claim 11, wherein the detector panel is configured to be positioned in closer proximity to the target region in the subject than the detector array while the detector array remains stationary relative to the target region during the scanning by the PET system.

13. The device of claim 8, wherein the detector panel is configured to be positioned below a patient table on which the subject lies during the scanning by the PET system.

14. The device of claim 8, wherein a surface of the detector panel that is to be positioned facing the subject during scanning by the PET system is substantially flat.

15. A method for enhancing a resolution of an image of a target region within a subject obtained using a positron emission tomography (PET) system, wherein the PET system includes a detector array including an array of gamma ray detectors that define a field of view and configured to detect at least one coincidence event and a control unit configured to be in communication with the detector array and configured to control the detector array, the method comprising:

providing a detector panel comprising an array of gamma ray detectors having higher resolutions than the gamma ray detectors of the detector array, the detector panel configured to be positioned in closer proximity to a patient table than the detector array and positioned outside the field of view defined by the detector array during at least a portion of scanning by the PET system, the detector panel configured to detect at least one coincidence event in cooperation with the detector array, and the detector panel configured to be in communication with the control unit and to be controlled by the control unit to operate in cooperation with the detector array.

16. The method of claim 15, further comprising:

positioning the detector panel in closer proximity to the patient table than the detector array and outside the field of view defined by the detector array during at least a portion of scanning by the PET system;

detecting the at least one coincidence event using the detector array and the at least one coincidence event using the detector panel in cooperation with the detector array; and reconstructing an image of the target region of the subject using the at least one coincidence event detected by the detector array combined with the at least one coincidence event detected by the detector panel.

17. The method of claim 16, wherein providing a detector panel further comprises providing the detector panel that includes an outsert configured to be positioned outside the field of view defined by the detector array during entire scanning by the PET system.

18. The method of claim 17, further comprising:

providing at least one additional detector panel including an additional array of high-resolution gamma ray detectors;

positioning the additional detector panel in closer proximity to the patient table than the detector array and outside the field of view defined by the detector array during entire scanning by the PET system;

detecting at least one additional coincidence event using the at least one additional detector panel in cooperation with the detector array and the detector panel; and reconstructing an image of the target region of the subject using the at least one additional coincidence event combined with the at least one coincidence event detected by the detector array and the at least one coincidence event detected by the detector panel.

19. The method of claim 16, further comprising moving the detector panel across the field of view defined by the detector array during scanning by the PET system.

20. The method of claim 19, wherein positioning the detector panel further comprises positioning the detector panel in closer proximity to the target region than the detector array, and moving the detector panel further comprises moving the detector panel and the patient table such that the detector panel remains stationary relative to the target region during the scanning by the PET system.

* * * * *